United States Patent
Ohguri et al.

(10) Patent No.: US 9,569,829 B2
(45) Date of Patent: Feb. 14, 2017

(54) IMAGE PROCESSING APPARATUS, RADIATION IMAGING APPARATUS, CONTROL METHODS FOR THEM, GAIN IMAGE CREATION METHOD, RADIATION IMAGING SYSTEM, AND STORAGE MEDIUM

(71) Applicant: CANON KABUSHIKI KAISHA, Tokyo (JP)

(72) Inventors: Hirokazu Ohguri, Funabashi (JP); Shinya Katsumata, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/688,352

(22) Filed: Apr. 16, 2015

(65) Prior Publication Data

US 2015/0310597 A1 Oct. 29, 2015

(30) Foreign Application Priority Data

Apr. 25, 2014 (JP) ................. 2014-091999
Aug. 5, 2014 (JP) ................. 2014-159762

(51) Int. Cl.
| | |
|---|---|
| G06K 9/40 | (2006.01) |
| G06T 5/50 | (2006.01) |
| H04N 5/225 | (2006.01) |
| A61B 6/00 | (2006.01) |
| G06T 5/00 | (2006.01) |
| H04N 5/213 | (2006.01) |

(52) U.S. Cl.
CPC . *G06T 5/50* (2013.01); *A61B 6/00* (2013.01); *G06T 5/008* (2013.01); *H04N 5/2254* (2013.01); *H04N 5/2257* (2013.01); *G06T 2207/10116* (2013.01); *G06T 2207/20016* (2013.01); *G06T 2207/20216* (2013.01); *H04N 5/213* (2013.01)

(58) Field of Classification Search
CPC ............ G06T 5/001; G06T 5/002; G06T 5/20; G06T 5/50; G06T 2207/10116; G06T 2207/20216; G06T 2207/20182; H04N 5/213; H04N 5/3205; H04N 7/26888; H04N 1/4097
See application file for complete search history.

(56) References Cited

U.S. PATENT DOCUMENTS

| | | | | |
|---|---|---|---|---|
| 6,694,172 | B1 * | 2/2004 | Gagnon ................ | G01T 1/2928 250/363.02 |
| 7,095,039 | B2 * | 8/2006 | Murakoshi .......... | G01N 23/046 250/580 |

(Continued)

FOREIGN PATENT DOCUMENTS

| | | |
|---|---|---|
| JP | 2011-247605 A | 12/2011 |
| JP | 2011-249891 A | 12/2011 |

*Primary Examiner* — Amir Alavi
(74) *Attorney, Agent, or Firm* — Carter, DeLuca, Farrell & Schmidt, LLP

(57) ABSTRACT

An image processing apparatus comprising: an obtaining unit configured to obtain a plurality of radiation images that have been sensed without arranging an object and include a defect, and information about the defect included in the radiation images; and a generation unit configured to generate a sensitivity correction image not including the defect based on the plurality of radiation images and the information about the defect.

24 Claims, 24 Drawing Sheets

(56) References Cited

U.S. PATENT DOCUMENTS

| | | | | |
|---|---|---|---|---|
| 7,362,916 | B2* | 4/2008 | Yamazaki | H04N 5/32 |
| | | | | 348/246 |
| 9,064,302 | B2* | 6/2015 | Muraoka | A61B 6/507 |
| 2014/0254758 | A1* | 9/2014 | Saigusa | A61B 6/545 |
| | | | | 378/62 |
| 2014/0254760 | A1* | 9/2014 | Hiroike | A61B 6/54 |
| | | | | 378/62 |
| 2015/0055752 | A1* | 2/2015 | Takahashi | H04N 5/32 |
| | | | | 378/62 |
| 2015/0310597 | A1* | 10/2015 | Ohguri | H04N 5/2254 |
| | | | | 382/275 |
| 2015/0363926 | A1* | 12/2015 | Enomoto | A61B 6/4233 |
| | | | | 382/132 |

* cited by examiner

F I G. 20
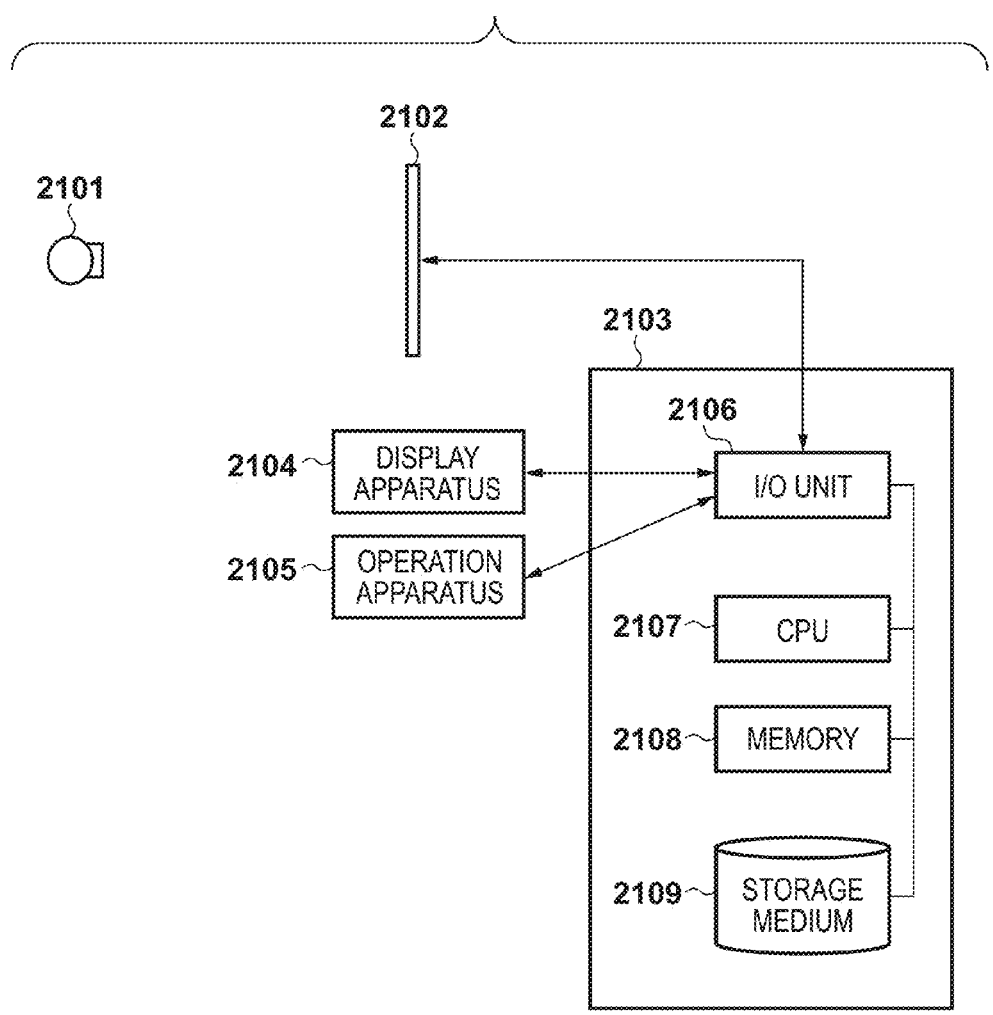

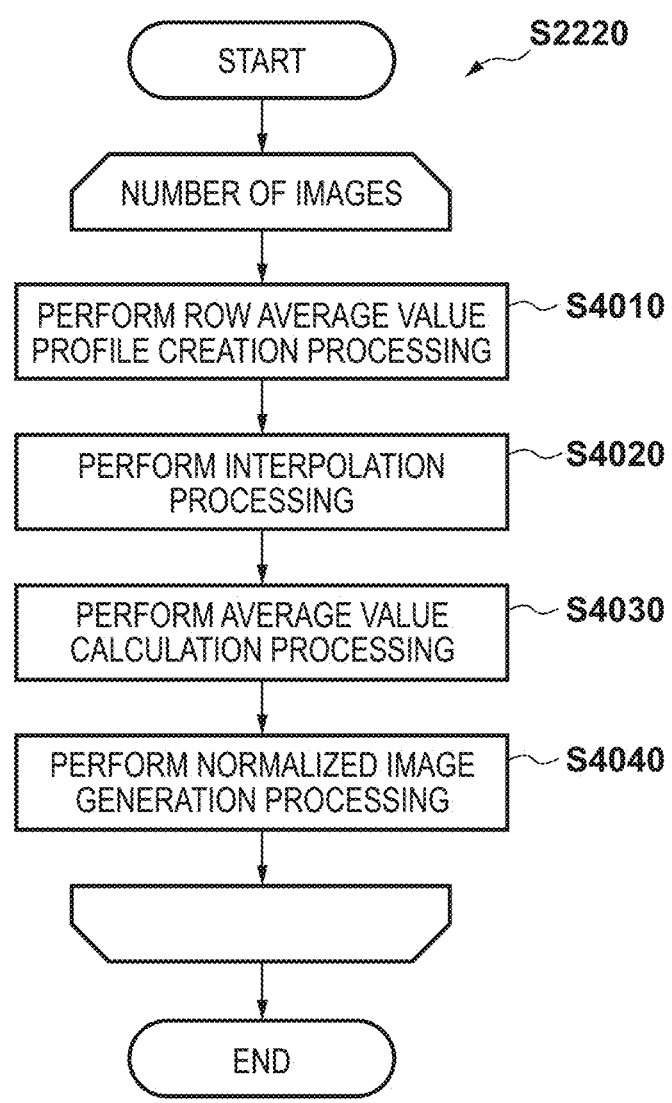

FIG. 26
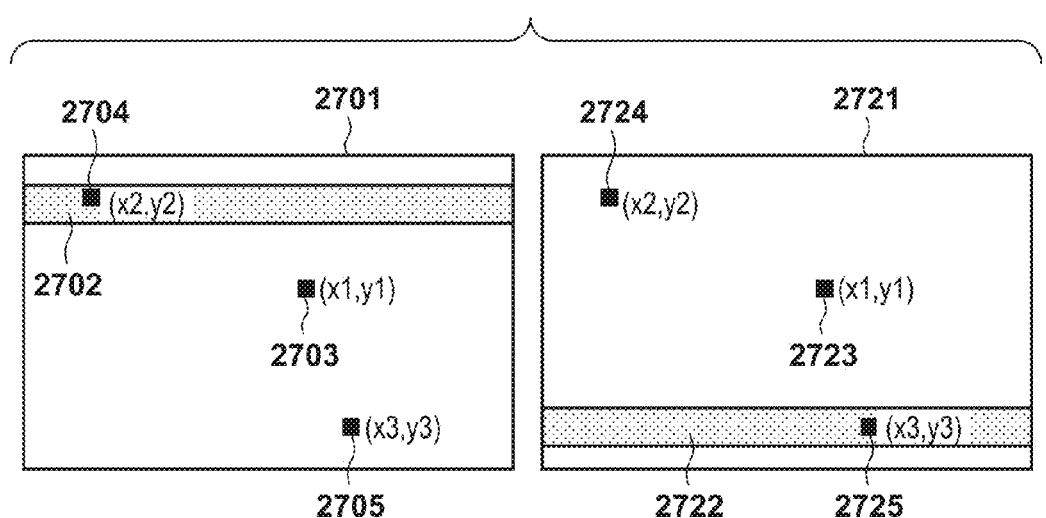

IMAGE PROCESSING APPARATUS, RADIATION IMAGING APPARATUS, CONTROL METHODS FOR THEM, GAIN IMAGE CREATION METHOD, RADIATION IMAGING SYSTEM, AND STORAGE MEDIUM

BACKGROUND OF THE INVENTION

Field of the Invention

The present invention relates to an image processing apparatus, a radiation imaging apparatus, control methods for them, a gain image creation method, a radiation imaging system, and a storage medium.

Description of the Related Art

Digital radiation imaging apparatuses and radiation imaging systems using these apparatuses have been commercialized. The digital radiation imaging apparatus irradiates an object with a radiation from a radiation irradiation source, and digitizes a radiation image serving as the intensity distribution of the radiation having passed through the object. Then, the apparatus performs necessary image processing on the digital radiation image, generating a clearer radiation image.

Recently, there are also implemented radiation imaging apparatuses and radiation imaging systems in which the radiation imaging apparatus itself can detect the start of irradiation with a radiation from a radiation generation apparatus to obviate the need for the connection between the radiation imaging apparatus and the radiation generation apparatus, and further improve installation, handling, and the like.

Japanese Patent Laid-Open Nos. 2011-247605 and 2011-249891 disclose methods of waiting for irradiation while sequentially selecting the respective scanning lines of a radiation imaging apparatus and switching the ON state/OFF state, and upon detecting a change of a current flowing inside the apparatus, detecting the start of irradiation with a radiation. According to this method, some of charges generated by irradiation with a radiation leak from a pixel corresponding to a scanning line on which scanning was stopped upon detecting the start of irradiation by the radiation imaging apparatus after the start of irradiation with the radiation. As a result, a linear or wedged defect may be generated in a radiation image.

Of processes from imaging to image obtainment, gain correction processing is generally performed on an obtained radiation image, in order to correct variations of the gains (sensitivities) of respective pixels arising from nonuniformity by the deposition process of a radiation detection sensor or the like, the presence of a singularly generated pixel with a different characteristic, aged deterioration or burn-in along with the use, or the like. In the gain correction processing, a radiation image (to be referred to as a gain image hereinafter) is used, which is obtained by uniformly irradiating the entire surface of the detection sensor with a radiation and imaging the surface at the time of installing a radiation imaging apparatus or periodically after installation. The output value of a radiation image obtained by irradiating an object with a radiation and imaging the object is divided by the output value of each corresponding pixel of the gain image.

However, when a gain image is sensed by the method of detecting the start of irradiation with a radiation from a change of an internal current, a linear or wedged defect is similarly generated even in the gain image. When the defect of the gain image is corrected by any image processing, a pixel in which the defect has been generated cannot correctly represent the original gain, and thus gain correction may not be performed correctly.

To solve the above problem, the present invention provides a technique for generating a defect-free sensitivity correction image even when irradiation with a radiation is detected based on a change of a current inside a radiation imaging apparatus and imaging is performed.

SUMMARY OF THE INVENTION

According to one aspect of the present invention, there is provided an image processing apparatus comprising: an obtaining unit configured to obtain a plurality of radiation images that have been sensed without arranging an object and include a defect, and information about the defect included in the radiation images; and a generation unit configured to generate a sensitivity correction image not including the defect based on the plurality of radiation images and the information about the defect.

Further features of the present invention will become apparent from the following description of exemplary embodiments with reference to the attached drawings.

BRIEF DESCRIPTION OF THE DRAWINGS

FIG. 20 is a view showing an example of the arrangement of an X-ray imaging system according to the fifth embodiment of the present invention;

FIG. 23 is a flowchart showing normalization processing;

FIG. 26 is a view for explaining creation of a gain image by composition of normalized images.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

The first embodiment will be explained first. This embodiment will describe in detail an example of generating a defect-free sensitivity correction image (gain image) by using two images including defects, and position information of these defects or the like.

<1. Arrangement of Radiation Imaging System>

Figure 1:
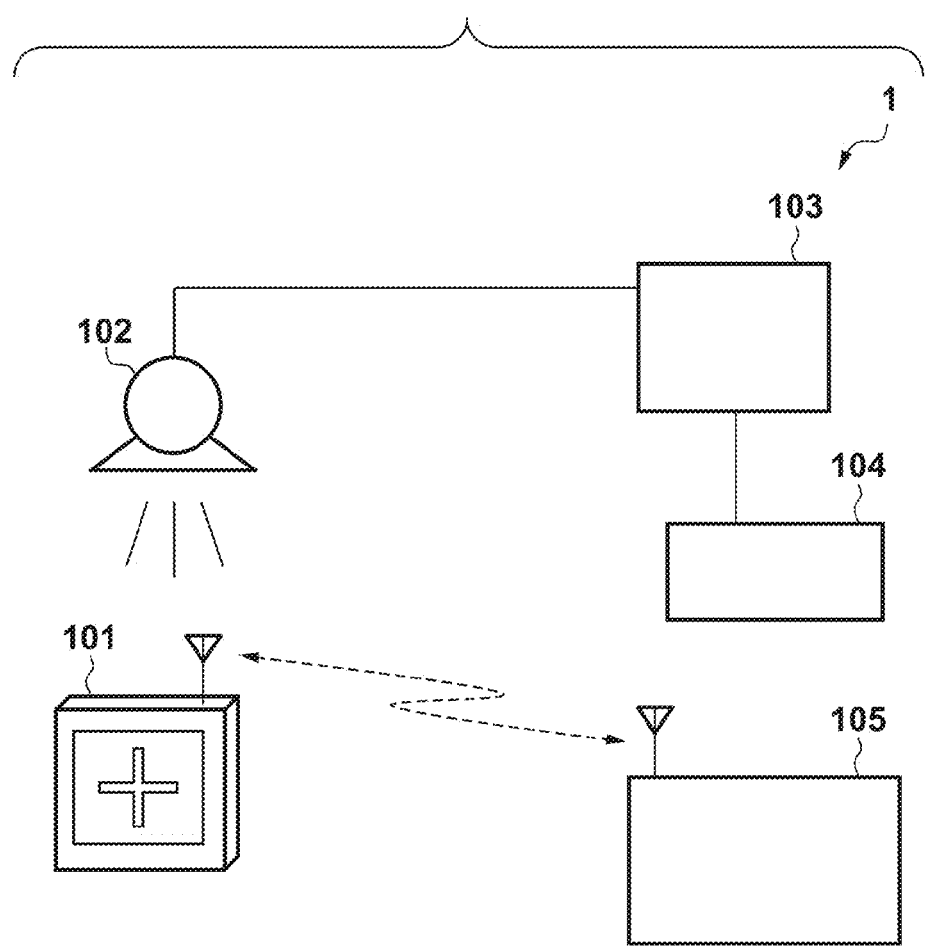
FIG. 1 is a view showing an example of the arrangement of a radiation imaging system according to the present invention.

FIG. 1 is a view showing an example of the arrangement of a radiation imaging system 1 according to the present invention. The radiation imaging system 1 includes a radiation imaging apparatus 101, a radiation tube 102, a radiation generation apparatus 103, a control apparatus 104, and an image processing apparatus 105.

The radiation imaging apparatus 101 incorporates a wireless transmission/reception device and can perform wireless communication with an external apparatus. The radiation tube 102 is installed to face the radiation imaging apparatus 101. When sensing a radiation image of an object, the object is arranged between the radiation tube 102 and the radiation imaging apparatus 101.

The control apparatus 104 controls the radiation generation apparatus 103. The image processing apparatus 105 incorporates a wireless transmission/reception device and can perform wireless communication with an external apparatus. A personal computer is generally used as the image processing apparatus 105. The image processing apparatus 105 issues an operation instruction to the radiation imaging apparatus 101 and acquires the state of the radiation imaging apparatus 101. Further, the image processing apparatus 105 performs image processing, image save, image display, and the like. The radiation imaging apparatus 101 and the image processing apparatus 105 perform exchange of information and transmission/reception of data via the wireless communication interfaces of communication units. The communication between the radiation imaging apparatus 101 and the image processing apparatus 105 may be performed via a wireless access point or the like, or wired connection using a physical cable.

<2. Arrangement of Radiation Imaging Apparatus>

Figure 2:
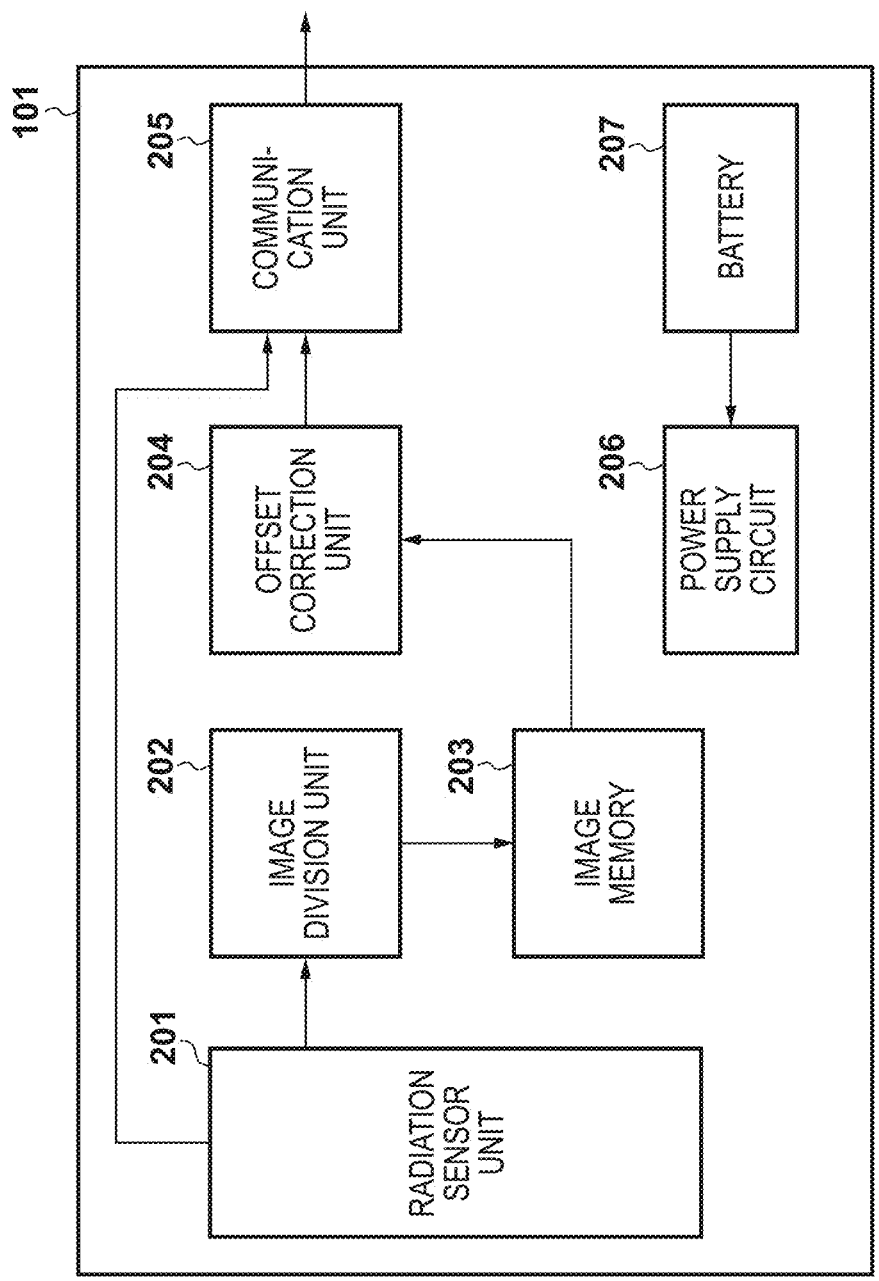
FIG. 2 is a block diagram showing an example of the arrangement of a radiation imaging apparatus according to the first embodiment of the present invention.

FIG. 2 is a block diagram showing an example of the internal arrangement of the radiation imaging apparatus 101. The radiation imaging apparatus 101 includes a radiation sensor unit 201, an image division unit 202, an image memory 203, an offset correction unit 204, a communication unit 205, a power supply circuit 206, and a battery 207 for wireless operation.

Image data output from the radiation sensor unit 201 is divided into a plurality of reduced images by the image division unit 202, and these reduced images are temporarily saved in the image memory 203. As image data, a plurality of radiation reduced images obtained by irradiation with a radiation, and a plurality of offset reduced images obtained without irradiation with a radiation are saved. The image memory 203 has a capacity enough to simultaneously hold at least these images. A volatile memory with a high access speed, such as a DRAM (Dynamic Random Access Memory), is often used as the image memory 203, but a non-volatile memory such as a flash memory may also be used.

The offset correction unit 204 performs offset correction processing by reading out radiation reduced images and offset reduced images from the image memory 203, and performing subtraction between corresponding images. The radiation sensor unit 201 holds information (defect correction information) for correcting a defect generated in an image by an imaging method to be performed in this embodiment. The defect correction information can also be held in the image memory 203. The communication unit 205 transmits the defect correction information and divided images to the image processing apparatus 105. The communication unit 205 includes a wireless communication interface, a wired communication interface, and a switching circuit for these interfaces. Also the communication unit 205 includes a cable connection unit for wired communication.

<3. Arrangement of Radiation Sensor Unit>

Figure 3:
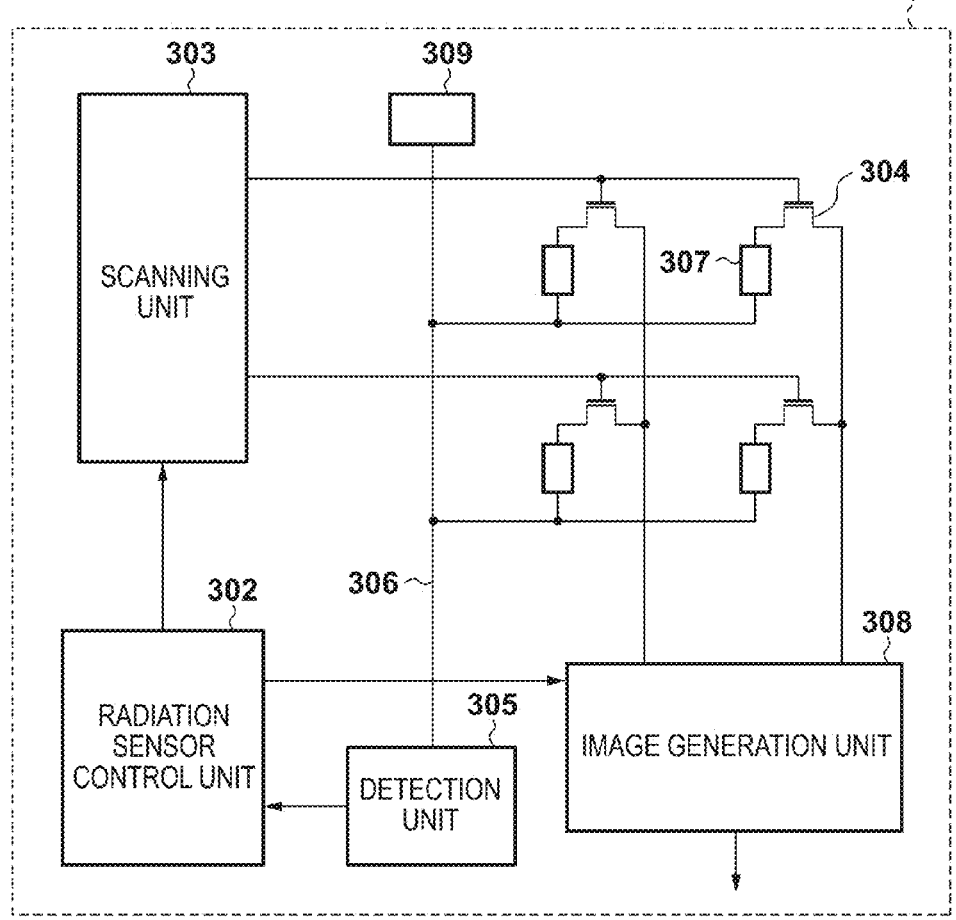
FIG. 3 is a diagram showing an example of the arrangement of a radiation sensor unit according to the present invention.

FIG. 3 shows an outline of the radiation sensor unit 201 in the radiation imaging apparatus 101. Although only a circuit of pixels of 2 rows×2 columns is illustrated for simplicity, a sensor having pixels of several thousand rows× several thousand columns is generally used recently. Note that the present invention does not limit the number of rows, the number of columns, and the number of pixels. The radiation sensor unit 201 includes a radiation sensor control unit 302, a scanning unit 303, TFTs (Thin Film Transistors) 304, a detection unit 305, a bias line 306, photoelectric converters 307, an image generation unit 308, and a bias power supply 309.

Upon receiving an imaging preparation start instruction from the image processing apparatus 105, the radiation imaging apparatus 101 operates the power supply circuit 206 and the like to make preparations, and then transits to an image sensing state through a state (called a radiation irradiation detection state) in which irradiation with a radiation is detected. The radiation irradiation detection state will be explained.

Figure 4:
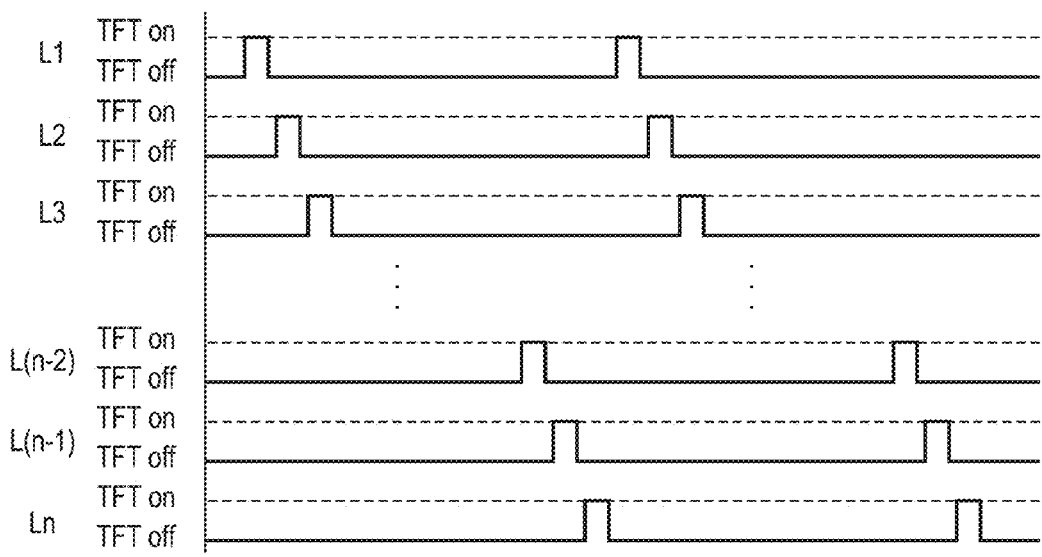
FIG. 4 is a chart showing an example of the scanning order of the radiation sensor unit according to the present invention.
Figure 5:
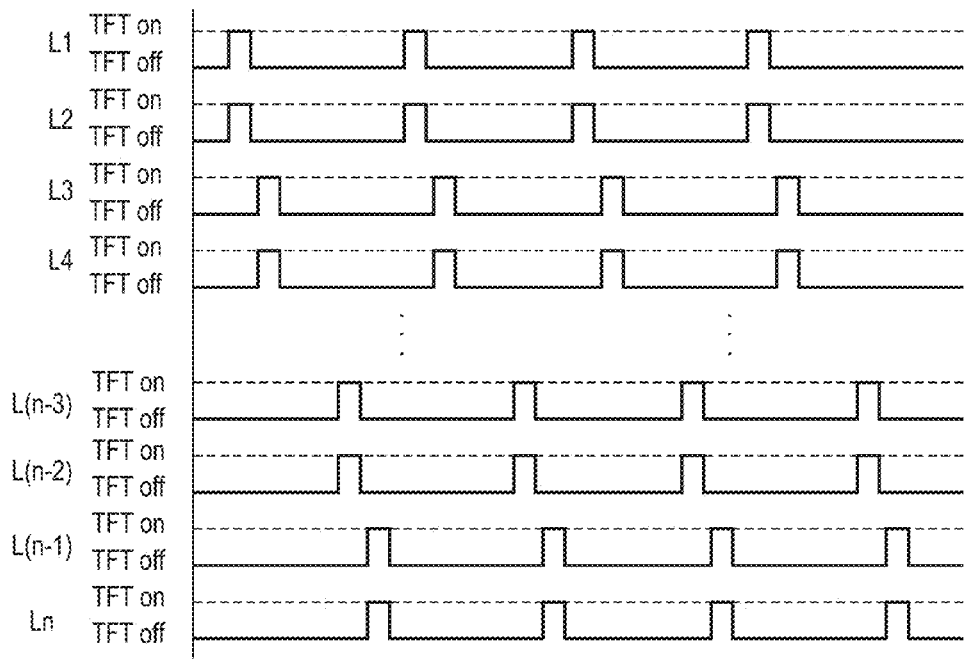
FIG. 5 is a chart showing an example of the scanning order of the radiation sensor unit according to the present invention.
Figure 6:
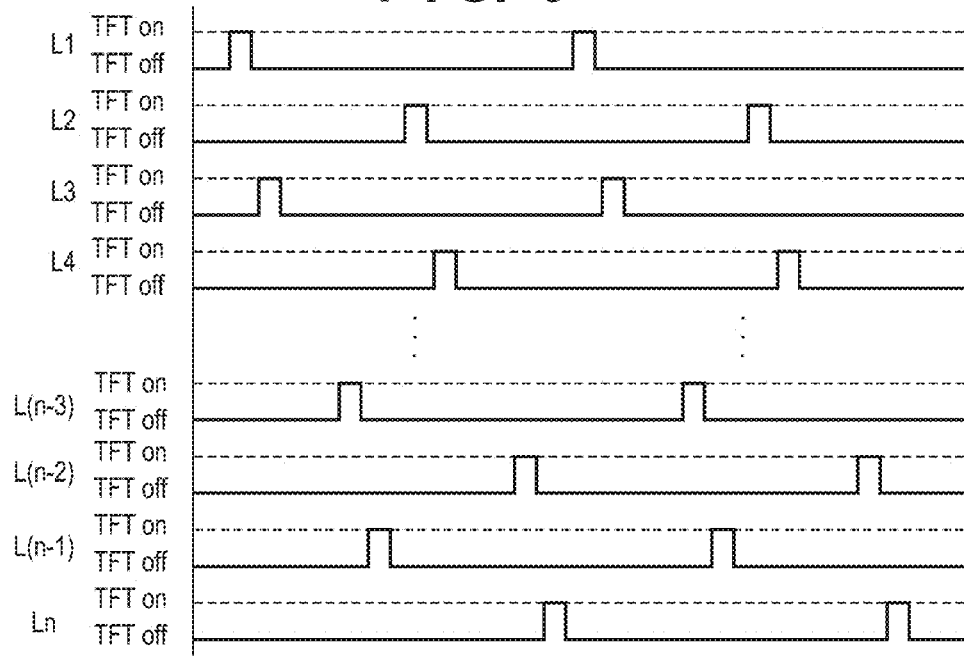
FIG. 6 is a chart showing an example of the scanning order of the radiation sensor unit according to the present invention.

The radiation sensor control unit 302 drives the scanning unit 303 to perform scanning of sequentially turning on the TFTs 304 for respective rows in accordance with a predetermined condition. That is, sensors are sequentially selected in the row direction to switch the ON state/OFF state. The order of scanning, the number of rows on which the TFTs are simultaneously turned on, and the like are not limited. FIGS. 4, 5, and 6 show examples of the scanning order of the radiation sensor unit having scanning lines L1 to Ln of n rows.

The TFTs may be turned on row by row from the row of the upper end of the radiation sensor unit 201 and sequentially scanned, as shown in FIG. 4, or the TFTs on a plurality of rows may be simultaneously turned on and sequentially scanned, as shown in FIG. 5. Also, the TFTs may be scanned not sequentially but while skipping a predetermined number of rows, as shown in FIG. 6. Further, these scanning orders may be combined. Scanning continues until irradiation with a radiation is detected. Upon scanning all rows, scanning is performed again from a row that was scanned first.

While the scanning unit 303 is driven, the detection unit 305 detects a current flowing through the bias line 306 connected to the bias power supply 309, and converts it into a digital value. The image generation unit 308 reads out charges and generates a radiation image in synchronism with the operation of sequentially turning on the TFTs of the respective rows by the scanning unit 303. The bias power supply 309 supplies a bias voltage to the photoelectric converter 307.

<4. Arrangement of Detection Unit>

Figure 7:
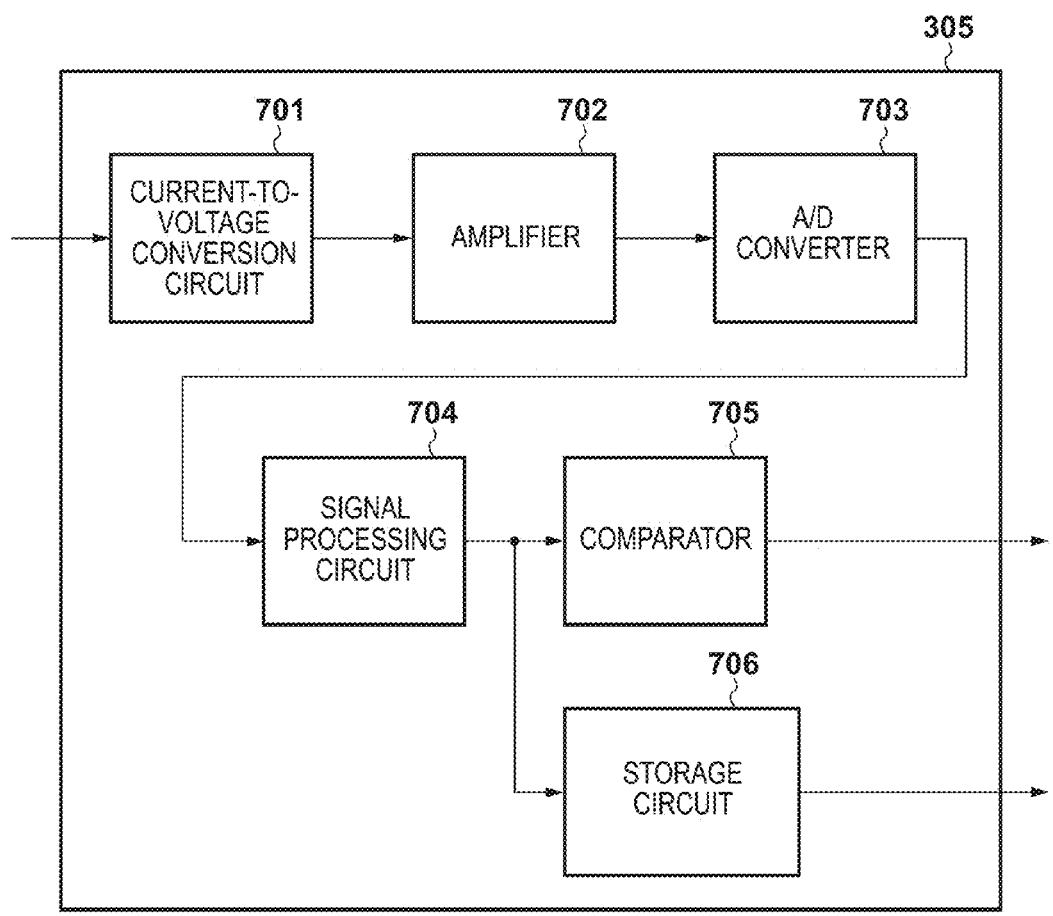
FIG. 7 is a block diagram showing an example of the arrangement of a detection unit according to the present invention.

FIG. 7 is a block diagram showing an example of the arrangement of the detection unit 305. The detection unit 305 includes a current-to-voltage conversion circuit 701, an amplifier 702, an A/D converter 703, a signal processing circuit 704, a comparator 705, and a storage circuit 706.

While the scanning unit 303 is driven, the detection unit 305 converts a current flowing through the bias line 306 connected to the bias power supply 309, into a digital value via the current-to-voltage conversion circuit 701, the amplifier 702, the A/D converter 703, and the signal processing circuit 704. The comparator 705 compares the digital value with a predetermined threshold, and outputs a signal representing the comparison result as a radiation irradiation detection signal to the radiation sensor control unit 302 and the like. When the digital value exceeds the predetermined threshold, the radiation sensor control unit 302 can determine that the current flowing through the bias line 306 has changed and irradiation with a radiation has been detected. The detection unit 305 sequentially stores digital values in the storage circuit 706. The state in which these operations are performed is equivalent to the radiation irradiation detection state.

The sampling frequency of the A/D converter 703 is arbitrary, and sampling may be performed a plurality of times at the timing when TFTs on a given scanning line are ON. However, it is desirable in data processing to finally perform averaging or the like, and convert a current into one digital value for one row or one scanning. In a state in which a given scanning line is selected, it is also desirable to obtain a digital value in a state in which the TFTs 304 are ON, and a digital value in a state in which they are OFF, and perform correlated double sampling of calculating the difference between these digital values. This can enhance resistance to external noise. Since the digital value is sequentially updated in synchronism with scanning, the storage circuit 706 desirably has a capacity capable of sequentially overwriting and updating the digital value and holding at least one digital value for all rows or all scans.

Upon irradiation with a radiation from the radiation tube 102, charges are generated in the photoelectric converter 307 by emission from a scintillator layer (not shown), and leak to the bias line 306. As a result, a current flowing through the bias line 306 changes. The detection unit 305 detects the change of the current through the above-mentioned circuits (current-to-voltage conversion circuit 701, amplifier 702, A/D converter 703, and signal processing circuit 704), and outputs an instruction to the radiation sensor control unit 302 to stop the above-mentioned scanning.

Accordingly, the radiation sensor unit 201 transits to a charge accumulation state arising from irradiation with a radiation. When scanning stops, the storage circuit 706 stops updating of the digital value and holds the digital value, and the radiation sensor control unit 302 stores, in a register (not shown), a scanning line number (scanning line position information) for specifying a scanning line on which scanning stopped. Note that the scanning line number (row number) need not always be used as long as the position at which scanning stopped can be specified.

This embodiment describes a detection method in which a change of a current flowing through the bias line 306 is used to detect irradiation with a radiation. However, the detection method is not limited to this as long as a current flowing inside the radiation imaging apparatus 101, the value of which changes in response to irradiation with a radiation, is used, and the position of a defect that is generated in a radiation image and arises from the radiation irradiation detection method is determined from the above-described position at which scanning was stopped. Also, a current flowing through the bias line 306 need not always be used.

Upon the lapse of a predetermined time after the transition to the charge accumulation state, the radiation sensor unit 201 performs an image readout operation. In the image readout operation, the scanning unit 303 scans TFTs on the respective rows while sequentially turning them on. In synchronism with this, the image generation unit 308 reads out charges and generates a radiation image. Thereafter, charges are accumulated without irradiation with a radiation, and the image readout operation is performed again, generating an offset image.

Figure 8:
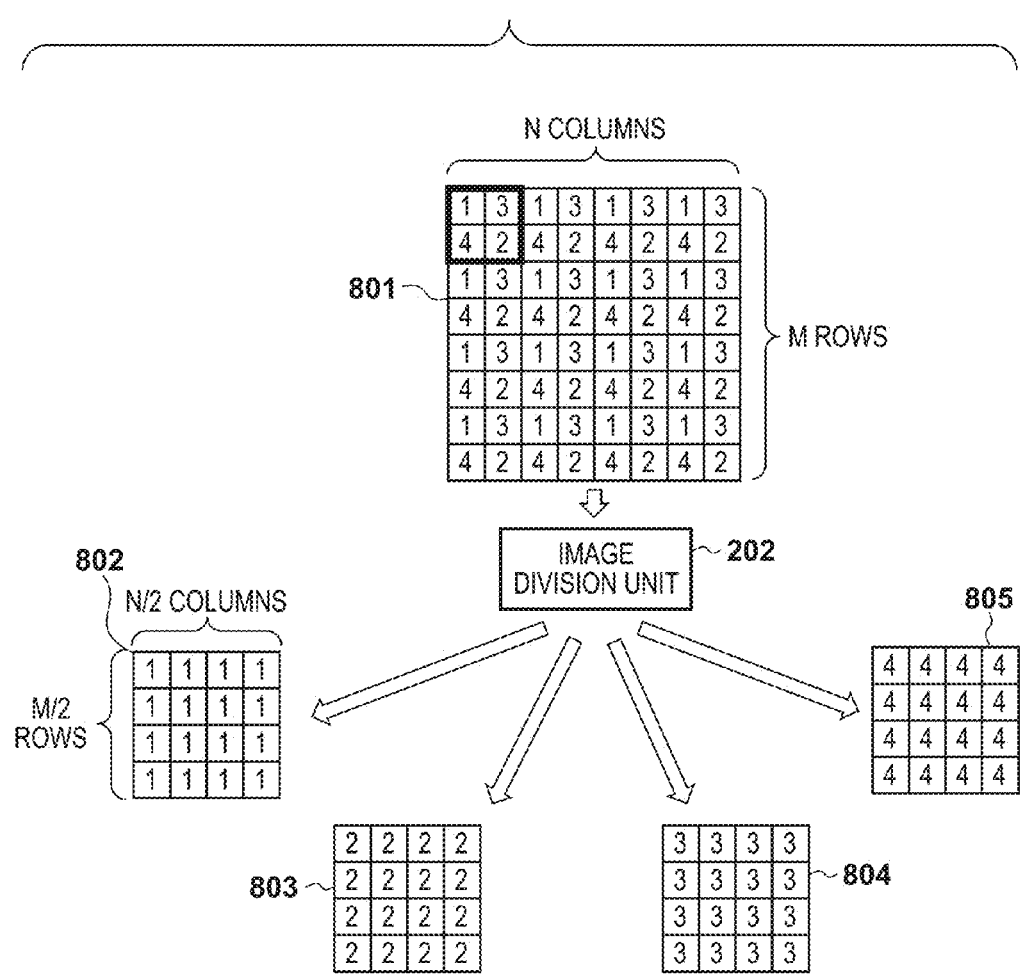
FIG. 8 is a view showing an example of an image division method according to the present invention.
Figure 9:
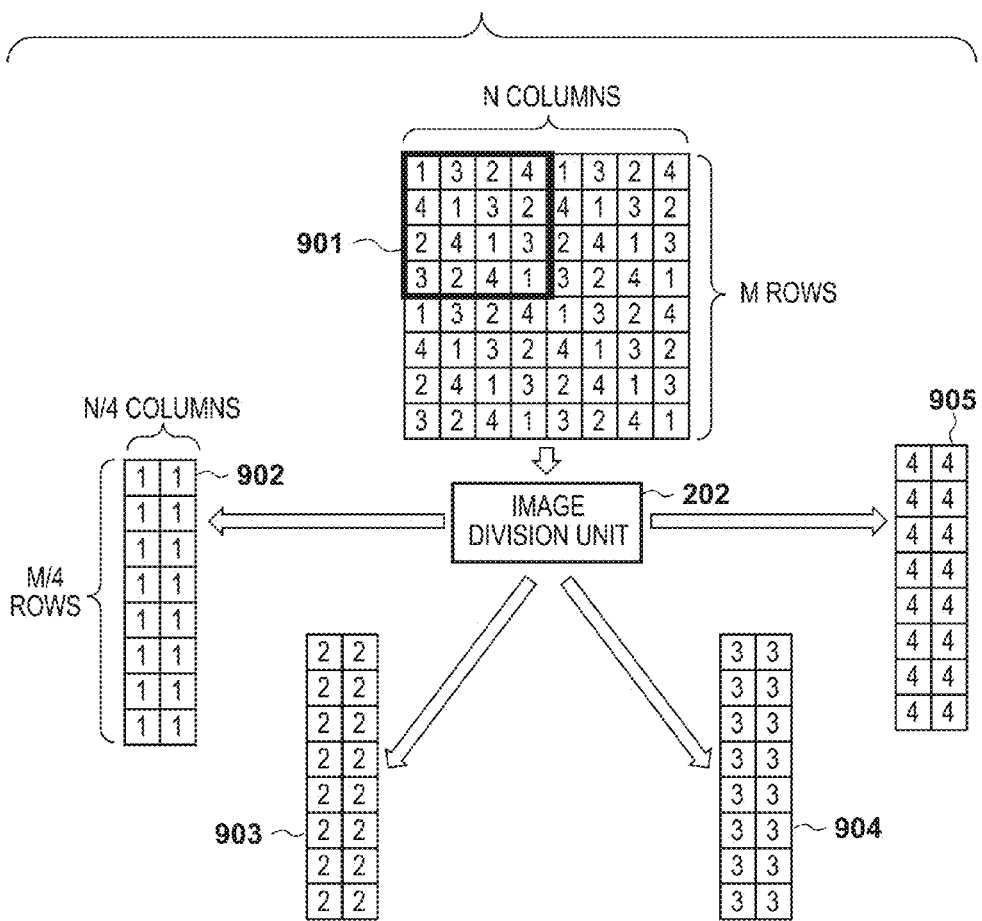
FIG. 9 is a view showing an example of the image division method according to the present invention.

FIGS. 8 and 9 show states of division of a full image by the image division unit 202 in the radiation imaging apparatus 101. FIGS. 8 and 9 show a case in which a full image 801 having pixels of M rows×N columns output from the radiation sensor unit 201 is input to the image division unit 202. The image division unit 202 divides the full image 801 into a plurality of reduced images based on a condition determined by the pixel position. In the example of FIG. 8, four pixels of 2 rows×2 columns are defined as a unit, and the full image 801 is divided based on the pixel position into four reduced images, that is, reduced image 1 (reduced image 802), reduced image 2 (reduced image 803), reduced image 3 (reduced image 804), and reduced image 4 (reduced image 805) each of M/2 rows×N/2 columns. These reduced images are saved in the image memory 203.

In the example of FIG. 9, 16 pixels of 4 rows×4 columns are defined as a unit, and a full image 901 is divided based on the pixel position into four reduced images, that is, reduced image 1 (reduced image 902), reduced image 2

(reduced image 903), reduced image 3 (reduced image 904), and reduced image 4 (reduced image 905) each of M rows×N/4 columns.

Note that the radiation image and the offset image are divided into the same number of reduced images each formed from the same number of pixels based on the same condition, and the reduced images are saved at respective save addresses in the image memory 203. The number of each reduced image indicates a turn in which the reduced image is sent from the radiation imaging apparatus 101 to the image processing apparatus 105.

After all radiation reduced images and offset reduced images are saved in the image memory 203, the offset correction unit 204 performs offset correction, and transfers the images to the communication unit 205. First, the offset correction unit 204 reads out radiation reduced image 1 and offset reduced image 1 from the image memory 203, and performs offset correction by subtracting offset reduced image 1 from radiation reduced image 1 between identical pixel positions. Subsequently, the offset correction unit 204 similarly performs offset correction between radiation reduced image 2 and offset reduced image 2, between radiation reduced image 3 and offset reduced image 3, and between radiation reduced image 4 and offset reduced image 4.

The communication unit 205 sequentially transmits the reduced images having undergone offset correction to the image processing apparatus 105. The communication unit 205 transmits defect correction information to the image processing apparatus 105 together with the images. In this embodiment, the defect correction information includes a digital value held in the storage circuit 706, and scanning line position information.

<5. Arrangement of Image Processing Apparatus>

Figure 10:
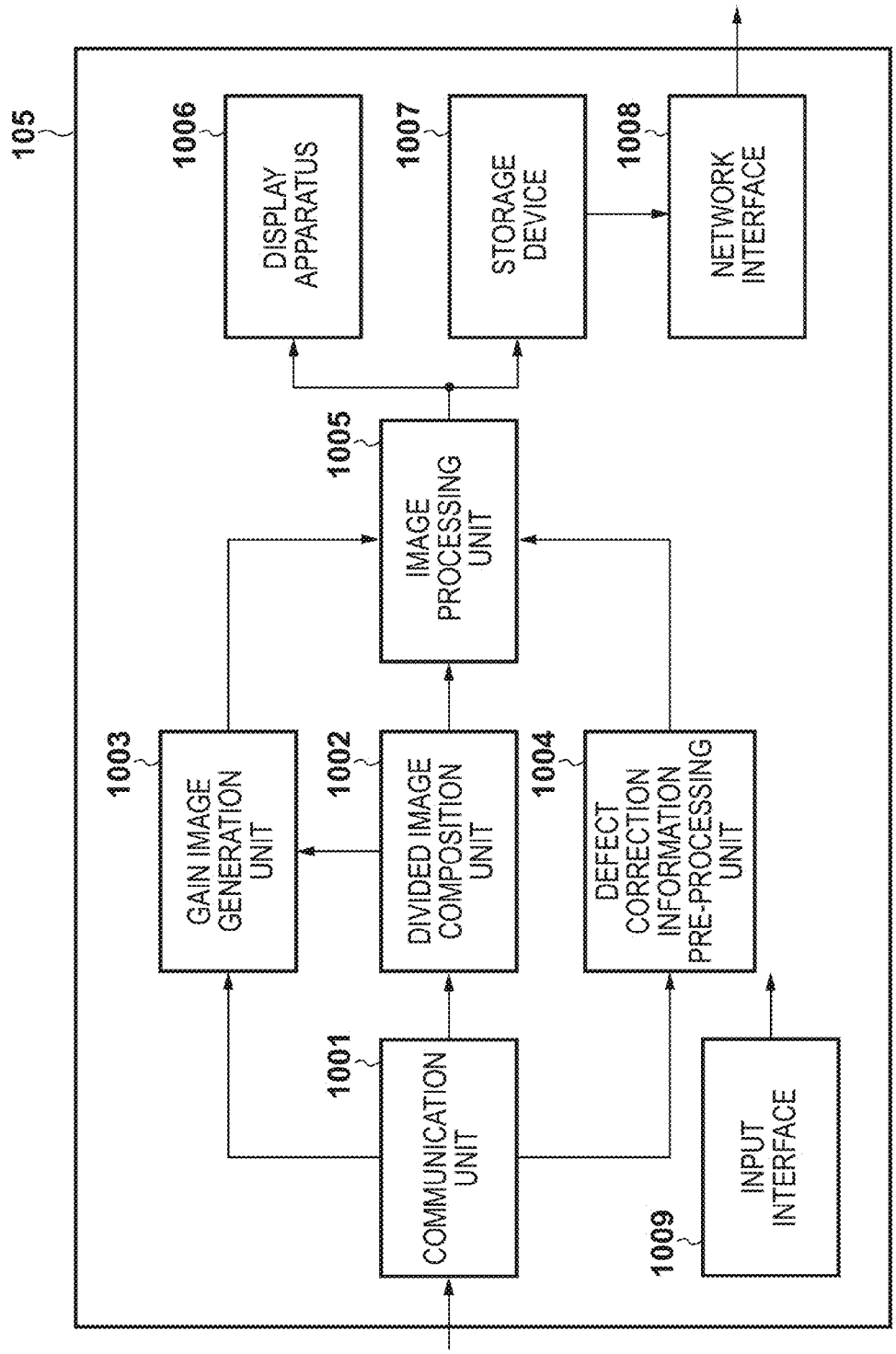
FIG. 10 is a block diagram showing an example of the arrangement of an image processing apparatus according to the first embodiment of the present invention.

FIG. 10 is a block diagram showing an example of the internal arrangement of the image processing apparatus 105. The image processing apparatus 105 includes a communication unit 1001, a divided image composition unit 1002, a gain image generation unit 1003, a defect correction information pre-processing unit 1004, an image processing unit 1005, a display apparatus 1006, a storage device 1007, a network interface 1008, and an input interface 1009.

The communication unit 1001 receives image data, and defect correction information including a digital value and scanning line position information from the radiation imaging apparatus 101, and exchanges operation instructions and operation states with the radiation imaging apparatus 101. The divided image composition unit 1002 performs necessary enlargement processing such as squaring on reduced image 1 that has been received from the radiation imaging apparatus 101 and has undergone offset correction, thereby generating a primary preview image. Upon receiving reduced image 2 having undergone offset correction, the divided image composition unit 1002 performs necessary enlargement processing such as squaring using reduced image 1 and reduced image 2 having undergone offset correction, thereby generating a secondary preview image with a different definition.

Subsequently, upon receiving reduced image 3 and reduced image 4 having undergone offset correction, the divided image composition unit 1002 reconstructs a full image before division by using all the reduced images having undergone offset correction. In this manner, the image processing apparatus 105 reconstructs a plurality of types of preview images having different definitions and an image before division based on a plurality of reduced images received from the radiation imaging apparatus 101.

The gain image generation unit 1003 generates a gain image to be used in gain correction processing. The defect correction information pre-processing unit 1004 performs pre-processing such as filter processing on defect correction information. The image processing unit 1005 performs, on a preview image and a full image, offset correction, correction using defect correction information having undergone pre-processing, gain correction using a gain image, correction processing such as defective pixel correction, and image processes such as sharpening and tone processing. The display apparatus 1006 displays a preview image and full image having undergone image processing. The storage device 1007 stores an image. An image is transferred from the storage device 1007 to an in-hospital server or the like via the network interface 1008 and an in-hospital network (not shown). The input interface 1009 accepts input of various kinds of information.

An image used to generate a gain image by the gain image generation unit 1003 is sensed upon adjusting the stop and the positional relationship between the radiation imaging apparatus 101 and the radiation tube 102 so that the entire surface of the radiation sensor unit 201 is uniformly irradiated with a radiation without arranging anything between the radiation imaging apparatus 101 and the radiation tube 102. Although the radiation dose for irradiation is arbitrary, it desirably falls within a range where the linearity between the irradiation amount of the radiation and the output value of the radiation sensor unit 201 is maintained.

For the radiation imaging apparatus 101, sensing of a radiation image of an object and sensing of a gain image are completely the same. In this embodiment, even images used to generate a gain image are sequentially transmitted as a plurality of reduced images obtained by dividing a full image, similarly to a radiation image of an object. However, it may also be configured not to divide a full image into reduced images when generating a gain image.

<6. Processing to be Executed by Radiation Imaging System>

Figure 11:
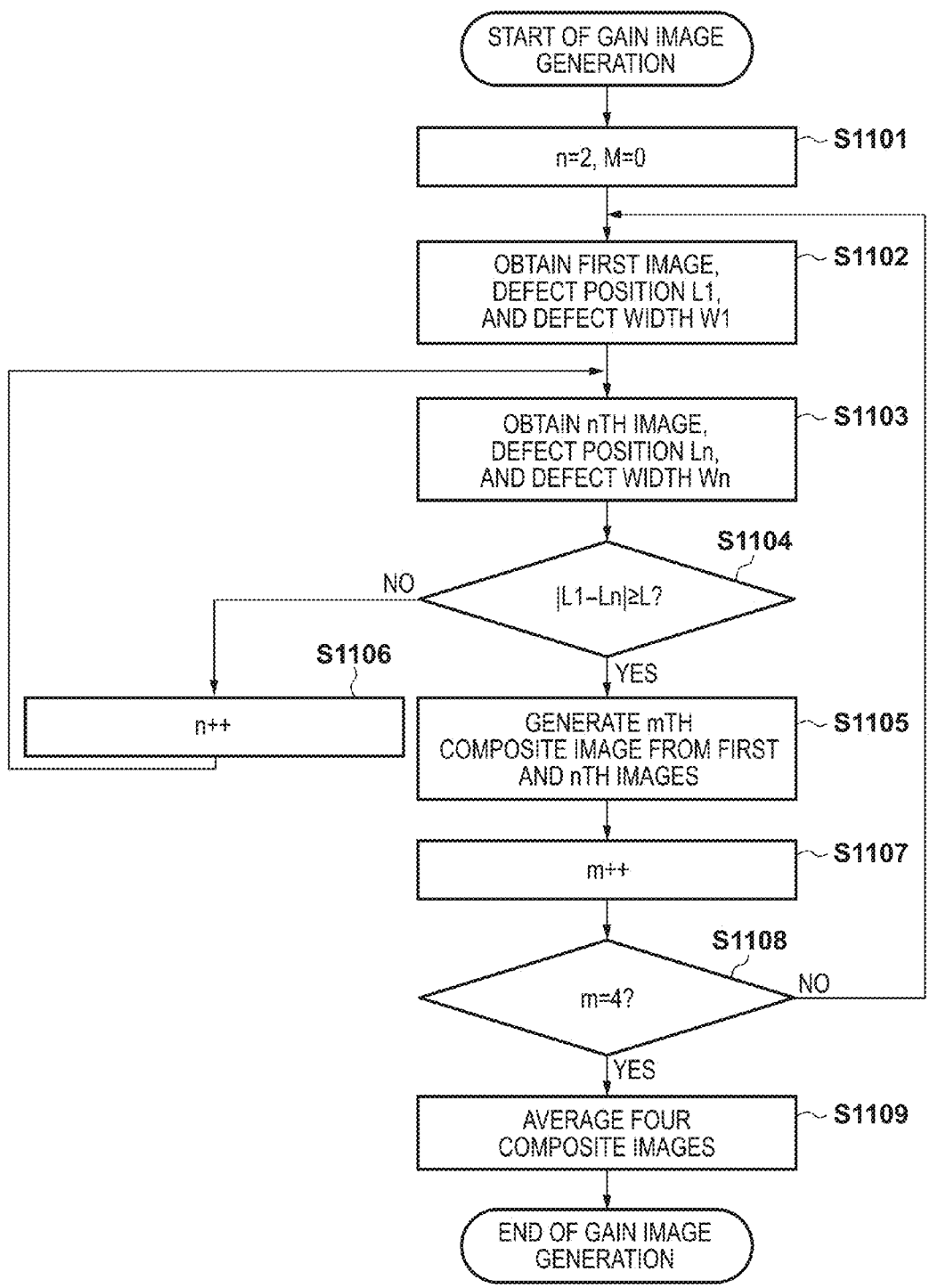
FIG. 11 is a flowchart showing gain image generation procedures according to the present invention.
Figure 12:
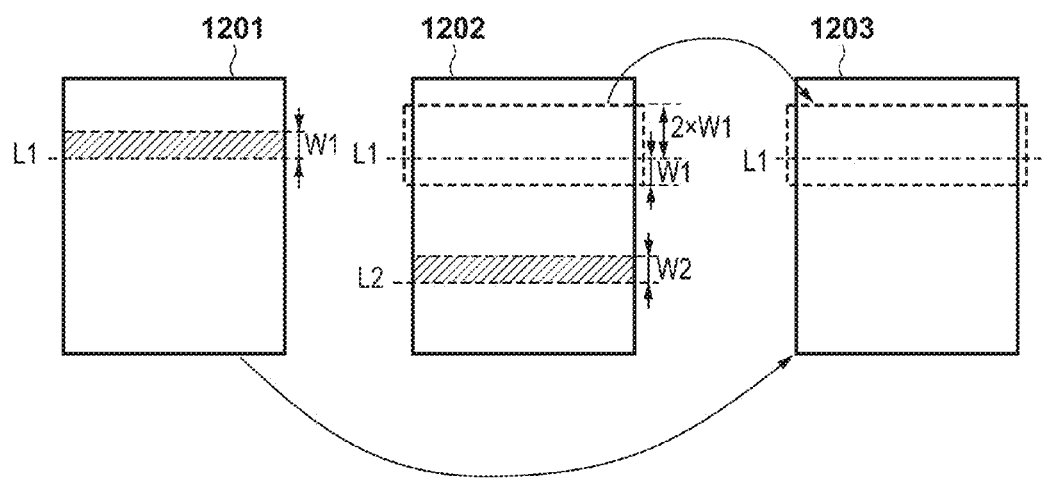
FIG. 12 is a view showing the state of gain image generation according to the present invention.

FIG. 11 is a flowchart showing gain image generation procedures according to this embodiment. FIG. 12 is a view showing the state of gain image generation. In step S1101, a variable n (n=2, 3, . . . ) and a variable m (m=0, 1, 2, . . . ) are initialized (n=2 and m=0 are set). In step S1102, the radiation imaging apparatus 101 senses the first image, and the image processing apparatus 105 obtains it. The divided image composition unit 1002 obtains a full image 1201 as shown in FIG. 12 by reconstruction from a plurality of reduced images. In addition, the divided image composition unit 1002 obtains a defect position L1 and defect width W1 of the first image from defect correction information (defect position information and defect width information) of the first image.

In step S1103, the radiation imaging apparatus 101 senses the second image. The divided image composition unit 1002 obtains a second full image 1202, and also obtains a defect position L2 and defect width W2 of the second image.

In step S1104, it is determined whether the distance between the defect position L1 and the defect position L2 on the image is much larger than the width defect W1 and the defect width W2. That is, it is determined whether inequality (1) is satisfied:

$$|L1-L2| \geq L \qquad (1)$$

where $L \gg W1, W2$.

If inequality (1) is satisfied, the process advances to step S1105. If inequality (1) is not satisfied, the process advances to step S1106. In step S1105, the divided image composition unit 1002 generates a defect-free composite image 1203 from the first and second images. Generation of the composite image is performed by replacing a portion of a width 2×W1 from the defect position L1 of the first image 1201 and a portion of the width W1 with an image of the same width at the same position in the second image 1202, as shown in FIG. 12.

In step S1106, n is incremented by one, and the process returns to step S1103 to sense the third image. The same processing is repeated to sense images until inequality (1) is satisfied. Inequality (1) is therefore generalized into:

$$|L1-Ln| \geq L (n=2,3,\ldots) \quad (2)$$

where L>>W1, Wn.

In step S1107, m is incremented by one. In step S1108, it is determined whether m=4. This embodiment assumes that four composite images are generated. If m<4, the process returns to step S1102 to repeat the procedures in steps S1102 to S1106.

In step S1109, after four defect-free composite images are generated, the composite images are averaged for noise reduction. The averaged composite image is obtained by outputting the average value of the pixel values of the four composite images for every pixel position of the four composite images. Then, the gain image generation processing ends.

The generated gain image is held in the image processing unit 1005 and used in gain correction every time a radiation image of an object is sensed. Note that a gain image may be held in the storage device 1007. FIG. 11 shows a sequence of generating a plurality of (four in this example) composite images and then averaging them. Alternatively, averaging may be executed every time a composite image is generated. In this case, the memory area for holding composite images can be reduced. Noise can be reduced by averaging. However, the number of composite images to be averaged in accordance with a request from the radiation imaging system is arbitrary, and it is also possible not to perform averaging.

Although L is decided based on W1 and Wn obtained from defect correction information in this embodiment, L can also be decided in advance from a condition such as the irradiation dose. In this case, L needs to be determined with a sufficient margin. A gain image is generated at the time of installing the radiation imaging apparatus 101, but may also be performed periodically such as every year.

Figure 13A:
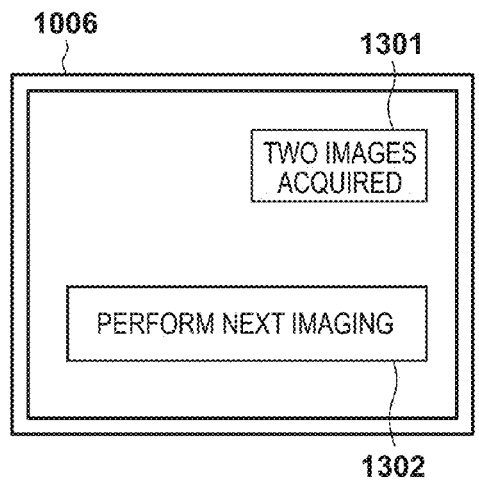
FIGS. 13A and 13B are views showing desired image display examples at the time of gain image generation according to the present invention.
Figure 13B:
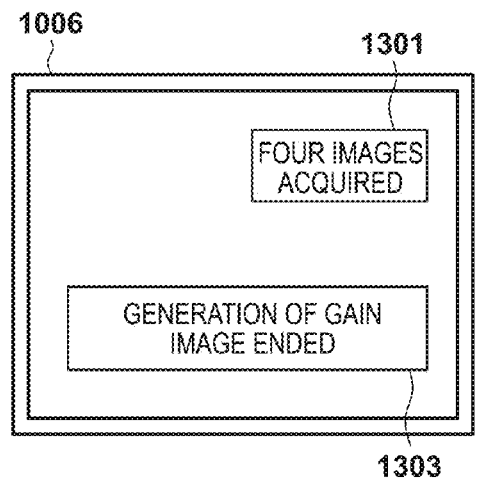

In a series of gain image generation operations, the user may designate the next operation through a GUI (Graphical User Interface) or the like displayed on the display apparatus 1006 of the image processing apparatus 105. At this time, as shown in FIGS. 13A and 13B, the image processing apparatus 105 may display information 1301 representing the number of successfully generated composite images, information 1302 representing that the next imaging needs to be performed, information 1303 representing that generation of a gain image has ended, and the like so that the user can comprehend them.

As described above, according to the first embodiment, even when irradiation with a radiation is detected based on a change of a current inside the radiation imaging apparatus and imaging is performed, a defect-free sensitivity correction image (gain image) can be generated.

Second Embodiment

Figure 14:
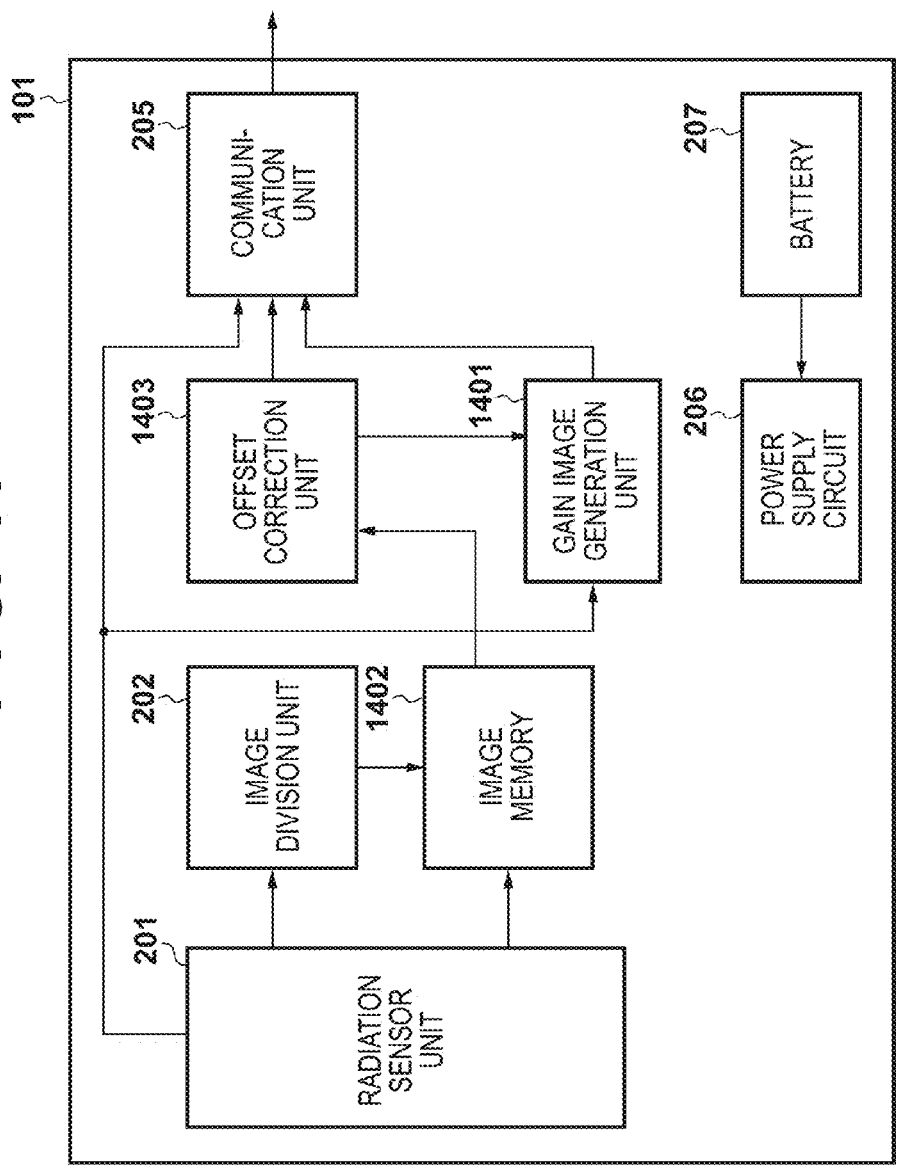
FIG. 14 is a block diagram showing an example of the arrangement of a radiation imaging apparatus according to the second embodiment of the present invention.

Next, the second embodiment will be explained.
<1. Arrangement of Radiation Imaging Apparatus>
FIG. 14 is a block diagram showing an example of the internal arrangement of a radiation imaging apparatus 101 according to the second embodiment. The radiation imaging apparatus 101 includes a radiation sensor unit 201, an image division unit 202, a communication unit 205, a power supply circuit 206, a battery 207, a gain image generation unit 1401, an image memory 1402, and an offset correction unit 1403.

In the first embodiment, a gain image is generated inside the image processing apparatus 105. To the contrary, in the second embodiment, a gain image is generated inside the radiation imaging apparatus 101. To do so, the radiation imaging apparatus 101 incorporates the gain image generation unit 1401. At the time of generating a gain image, an image is saved as a full image in the image memory 1402 without the intervention of the image division unit 202. The image memory 1402 therefore needs to temporarily hold a plurality of radiation reduced images, a plurality of offset reduced images, a radiation full image, and an offset full image. For this purpose, an image memory area with a capacity enough to simultaneously hold all the images may be prepared. However, the reduced images and full image need not be held simultaneously, so the same image memory area may be used. The offset correction unit 1403 can execute offset correction between reduced images and offset correction between full images.

Figure 15:
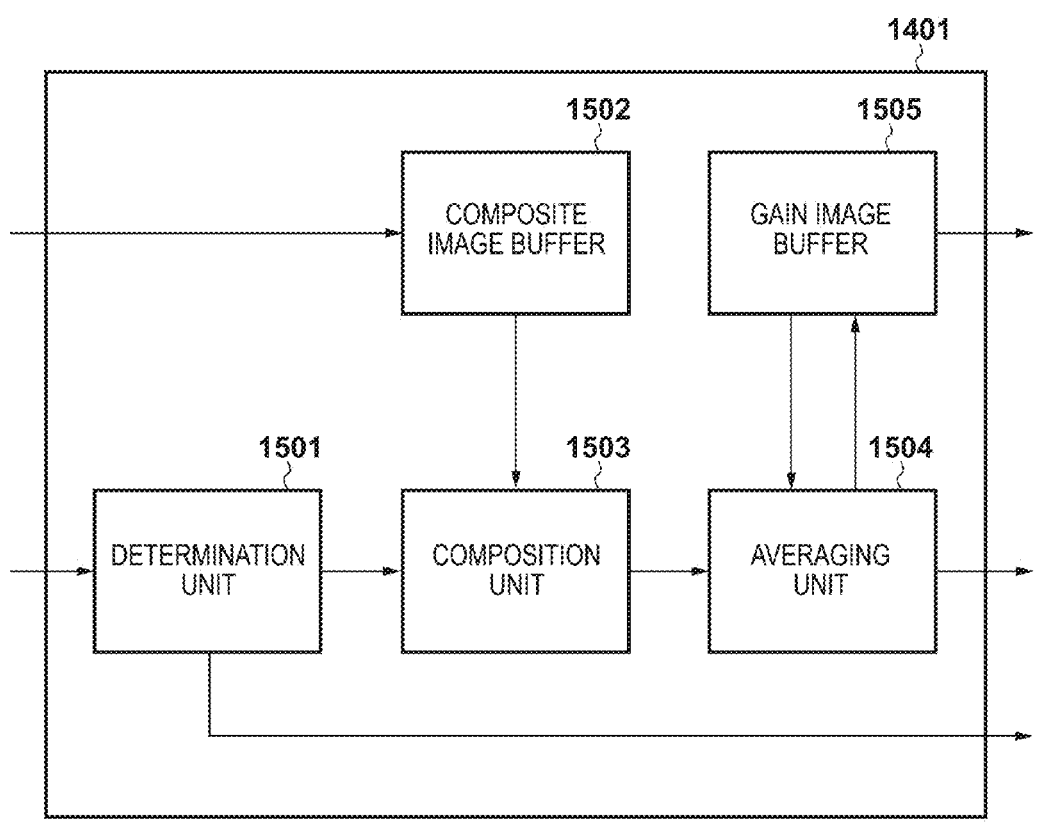
FIG. 15 is a block diagram showing an example of the arrangement of a gain image generation unit according to the second embodiment of the present invention.

<2. Arrangement of Gain Image Generation Unit>
FIG. 15 shows an example of the internal arrangement of the gain image generation unit 1401. The gain image generation unit 1401 includes a determination unit 1501, a composite image buffer 1502, a composition unit 1503, an averaging unit 1504, and a gain image buffer 1505.

Generation of a gain image starts, and the determination unit 1501 first obtains a defect position L1 and defect width W1 of the first image from defect correction information of the first image. At the same time, the first image is transferred from the offset correction unit 1403 to the composite image buffer 1502, and saved in an area for the first image. Then, the determination unit 1501 obtains a defect position L2 and defect width W2 of the second image from defect correction information of the second image.

The determination unit 1501 determines whether the defect position L1 and the defect position L2 satisfy inequality (2). That is, the determination unit 1501 determines whether a sensitivity correction image (gain image) can be generated. If inequality (2) is satisfied, the second image is saved in an area for the second image in the composite image buffer 1502. If inequality (2) is not satisfied, the determination unit 1501 notifies an image processing apparatus 105 via the communication unit 205 that the next imaging is necessary, and causes it to execute the next imaging.

If inequality (2) is satisfied, the composition unit 1503 reads out two images from the composite image buffer 1502, and generates a defect-free composite image. Composition processing is the same as that in the first embodiment. The composite image is sent to the averaging unit 1504. The second to fourth composite images are generated in the same way. The averaging unit 1504 saves the first composite image in the gain image buffer 1505 without any processing. For the second to fourth composite images, the averaging unit 1504 reads out an image from the gain image buffer 1505, performs averaging processing with the sent composite image, and writes back the image in the gain image buffer 1505. After the end of averaging processing for the four composite images, the determination unit 1501 notifies the image processing apparatus 105 via the communication unit 205 that the generation of the gain image has ended. Finally, the gain image is transmitted from the gain image buffer 1505 to the image processing apparatus 105 via the communication unit 205.

<3. Arrangement of Image Processing Apparatus>

Figure 16:
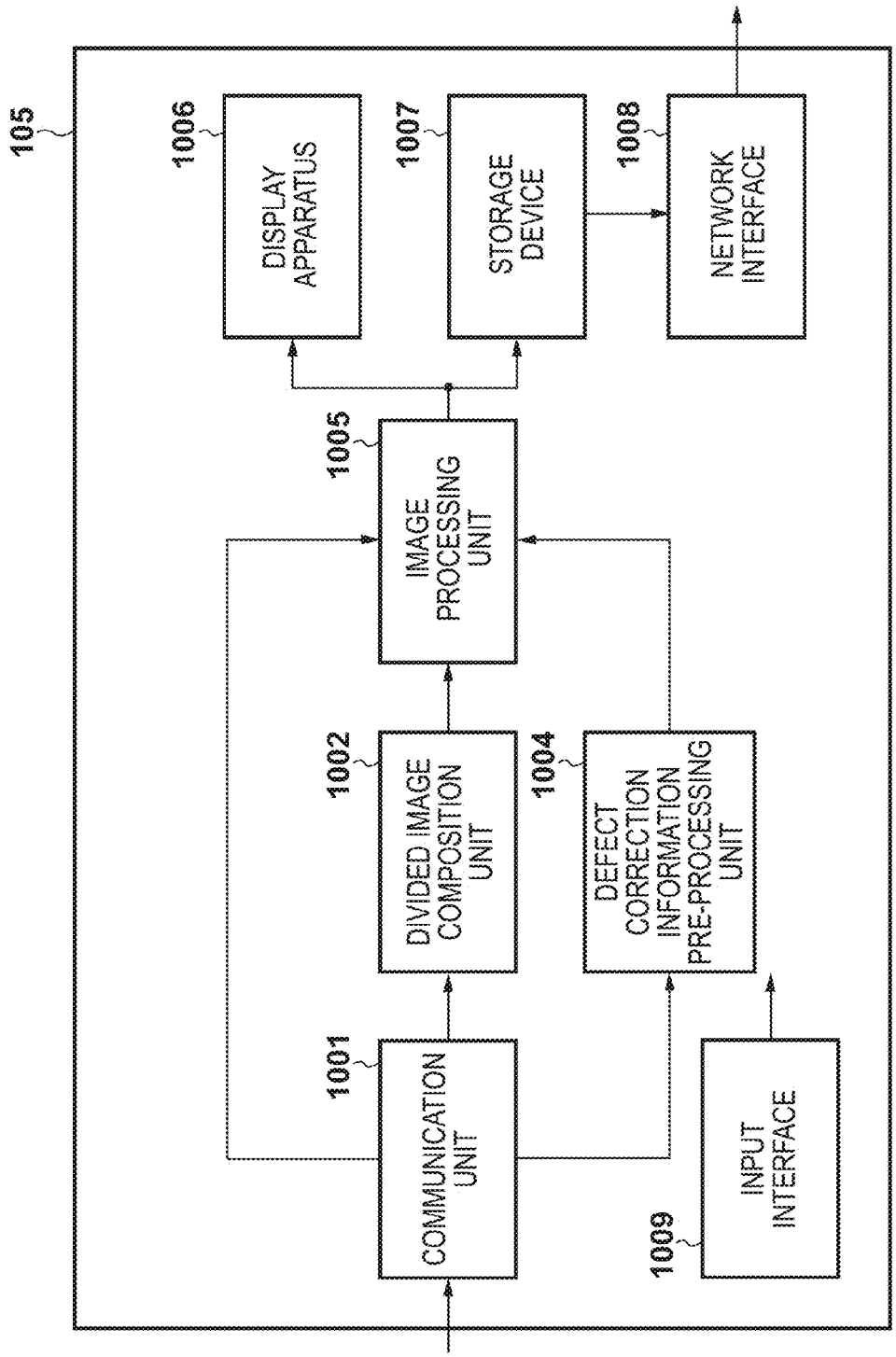
FIG. 16 is a block diagram showing an example of the arrangement of an image processing apparatus according to the second embodiment of the present invention.

FIG. 16 shows an example of the internal arrangement of the image processing apparatus 105 according to the second embodiment. The image processing apparatus 105 according to the second embodiment does not include the gain image generation unit 1003, unlike the first embodiment, but the remaining arrangement is the same as that described with reference to FIG. 10. A communication unit 1001 causes an image processing unit 1005 to hold a received gain image. The received gain image may be held in a storage device 1007. Gain correction is the same as that in the first embodiment. Notification to a user by a display apparatus 1006 is also the same as that in the first embodiment.

The composite image buffer 1502 and the gain image buffer 1505 in the gain image generation unit 1401 may use physically independent memories, or may use separate address areas on physically the same memory as the image memory 1402.

As described above, according to the second embodiment, even when irradiation with a radiation is detected based on a change of a current inside the radiation imaging apparatus and imaging is performed, a defect-free sensitivity correction image (gain image) can be generated.

Third Embodiment

Next, the third embodiment will be explained.

<1. Arrangement of Radiation Imaging Apparatus>

Figure 17:
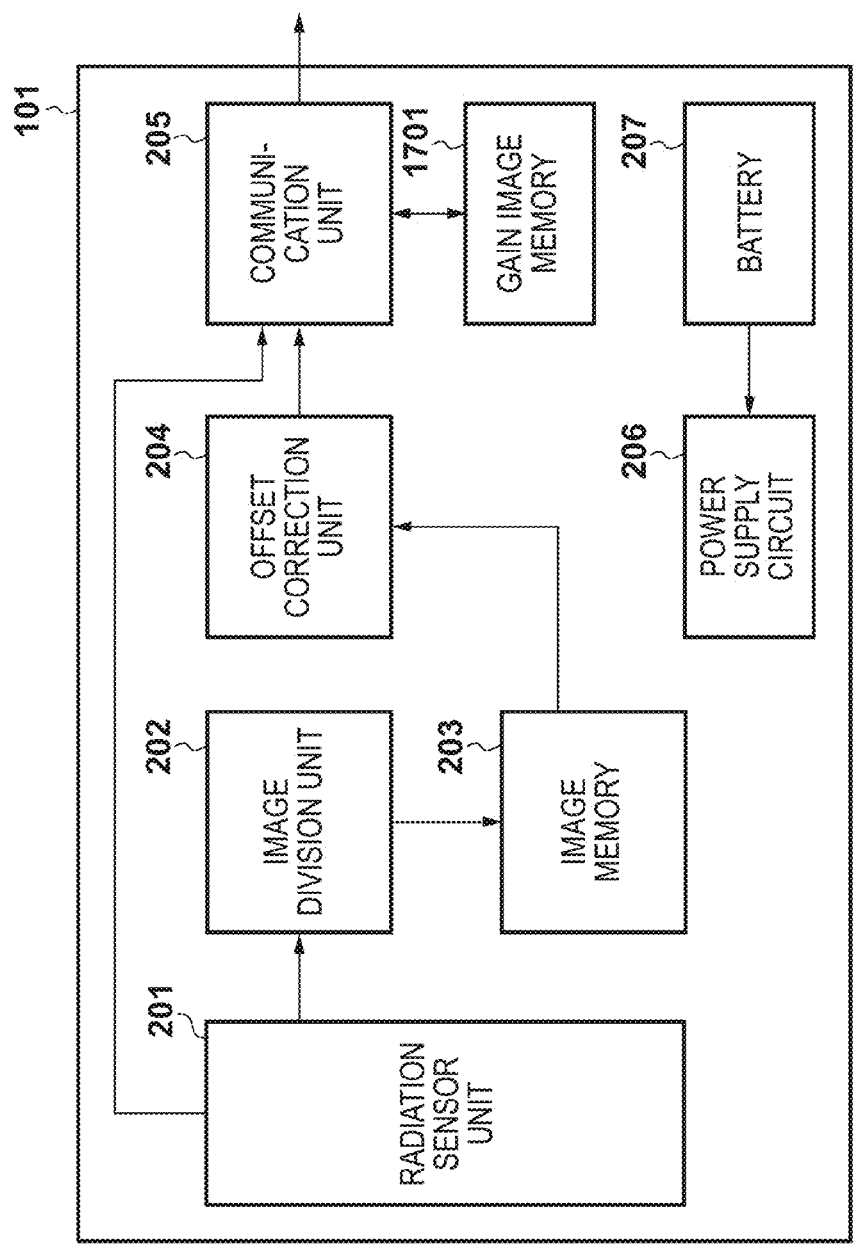
FIG. 17 is a block diagram showing an example of the arrangement of a radiation imaging apparatus according to the third embodiment of the present invention.

FIG. 17 is a block diagram showing an example of the internal arrangement of a radiation imaging apparatus 101 according to the third embodiment. The radiation imaging apparatus 101 according to the third embodiment further includes a gain image memory 1701, unlike the first embodiment, but the remaining arrangement is the same as that described with reference to FIG. 2. Processing up to generation of a gain image is the same as that in the first embodiment. In the third embodiment, a generated gain image is transmitted from an image processing apparatus 105 to the radiation imaging apparatus 101, and saved in the gain image memory 1701. The gain image memory 1701 is constituted by a non-volatile memory such as a flash memory.

<2. Processing Regarding Gain Image>

Figure 18:
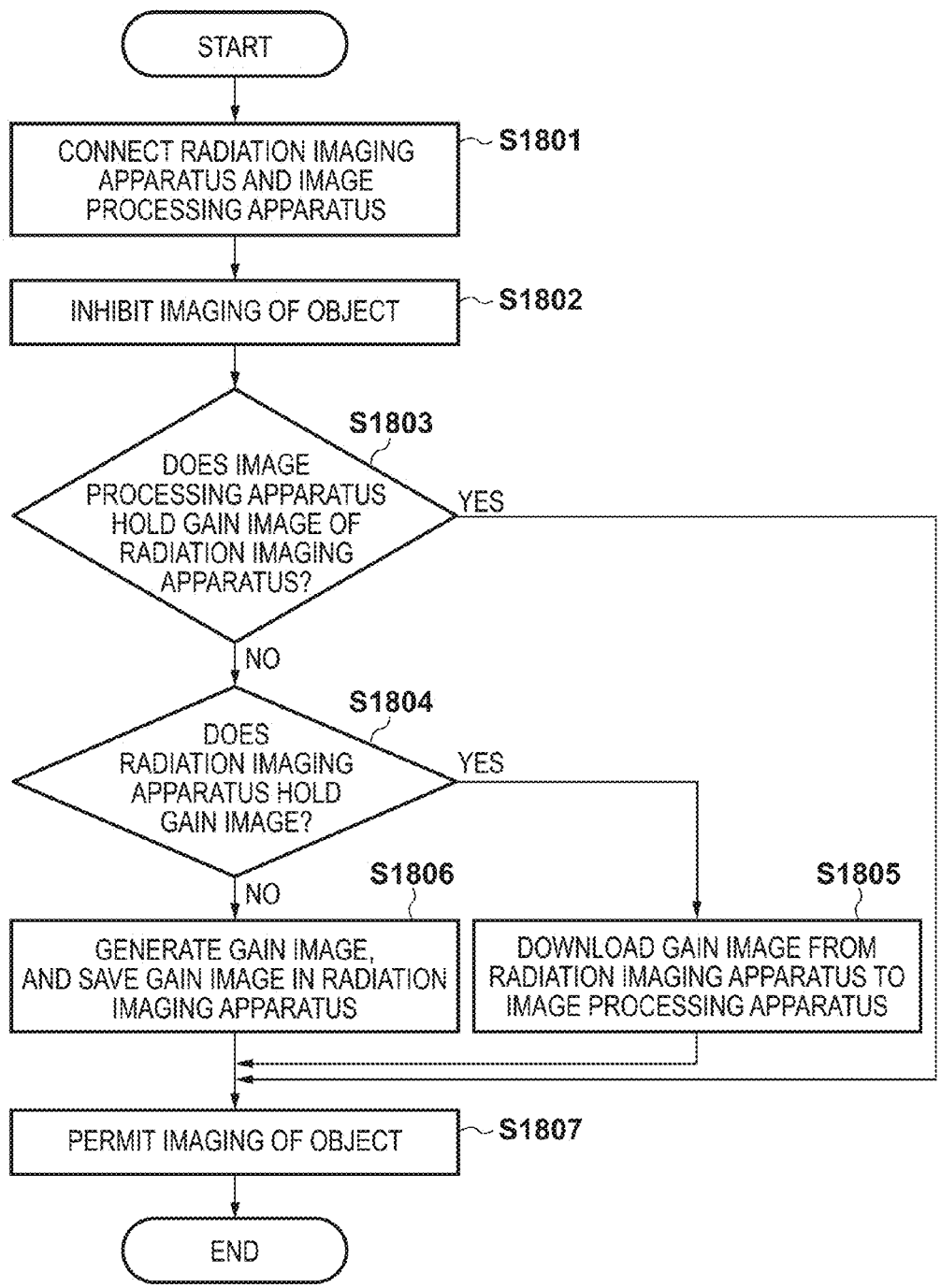
FIG. 18 is a flowchart showing the procedures of a determination operation regarding a gain image according to the third embodiment of the present invention.

FIG. 18 is a flowchart showing the procedures of processing regarding a gain image according to the third embodiment. First, an operation when the radiation imaging apparatus 101 is activated for the first time will be explained. In step S1801, communication connection between the radiation imaging apparatus 101 and the image processing apparatus 105 is established. In step S1802, the image processing apparatus 105 temporarily inhibits imaging of an object by the radiation imaging apparatus 101 during a determination operation of whether the radiation imaging apparatus has held a sensitivity correction image (gain image). In addition, the image processing apparatus 105 may output a display from which the user notices that imaging is inhibited.

In step S1803, the image processing apparatus 105 determines whether the gain image of the currently connected radiation imaging apparatus 101 has been held in an image processing unit 1005 or a storage device 1007. If it is determined that the gain image has been held, the process advances to step S1807. If it is determined that the gain image has not been held, the process advances to step S1804. Since the radiation imaging apparatus 101 is activated for the first time in this case, no gain image has been held, and the process advances to step S1804.

In step S1804, the radiation imaging apparatus 101 determines whether a gain image has been held in the gain image memory 1701. If it is determined that a gain image has been held, the process advances to step S1805. If it is determined that no gain image has been held, the process advances to step S1806.

In step S1805, the image processing apparatus 105 obtains the gain image from the radiation imaging apparatus 101. The process then advances to step S1807. In step S1806, the image processing apparatus 105 generates a gain image. The generation is the same as that described in the first embodiment. After the end of generating the gain image, the gain image is held in the image processing unit 1005 or the storage device 1007 inside the image processing apparatus 105, and is also transmitted to the radiation imaging apparatus 101. The radiation imaging apparatus 101 saves the received gain image in the gain image memory 1701.

In step S1807, the image processing apparatus 105 permits imaging of an object by the radiation imaging apparatus 101, and shifts to a state in which imaging of the object can be executed. Then, the respective processes of the flowchart in FIG. 18 end.

Next, an operation when the same radiation imaging apparatus 101 and image processing apparatus 105 as the previous ones are activated again will be explained. The processes in steps S1801 and S1802 are the same as those described above. However, the image processing apparatus 105 holds a gain image obtained by the radiation imaging apparatus 101, so YES in step S1803. Imaging is permitted in step S1807, and the process ends.

Further, an operation when the radiation imaging apparatus 101, and another image processing apparatus different from the image processing apparatus 105 are connected will be explained. Assume that the other image processing apparatus also has the same arrangement as that of the image processing apparatus 105. Since the other image processing apparatus does not hold the gain image of the radiation imaging apparatus 101, NO in step S1803 and the process advances to step S1804. Since the radiation imaging apparatus 101 has held the gain image in the gain image memory 1701, YES in step S1804 and the process advance to step S1805. In step S1805, the gain image held in the radiation imaging apparatus 101 is transmitted to the other image processing apparatus, and saved in the image processing unit 1005 or the storage device 1007.

In order to discriminate a radiation imaging apparatus corresponding to a gain image held in the image processing apparatus 105, identification information such as a unique number or symbol may be added to the radiation imaging apparatus to manage the radiation imaging apparatus, and this identification information may also be added to the gain image to manage the gain image. Generation of a gain image is performed by the image processing apparatus 105 in this embodiment, but may also be performed by the radiation imaging apparatus 101.

As described above, according to the third embodiment, even when irradiation with a radiation is detected based on a change of a current inside the radiation imaging apparatus and imaging is performed, a defect-free sensitivity correction image (gain image) can be generated.

Fourth Embodiment

Figure 19:
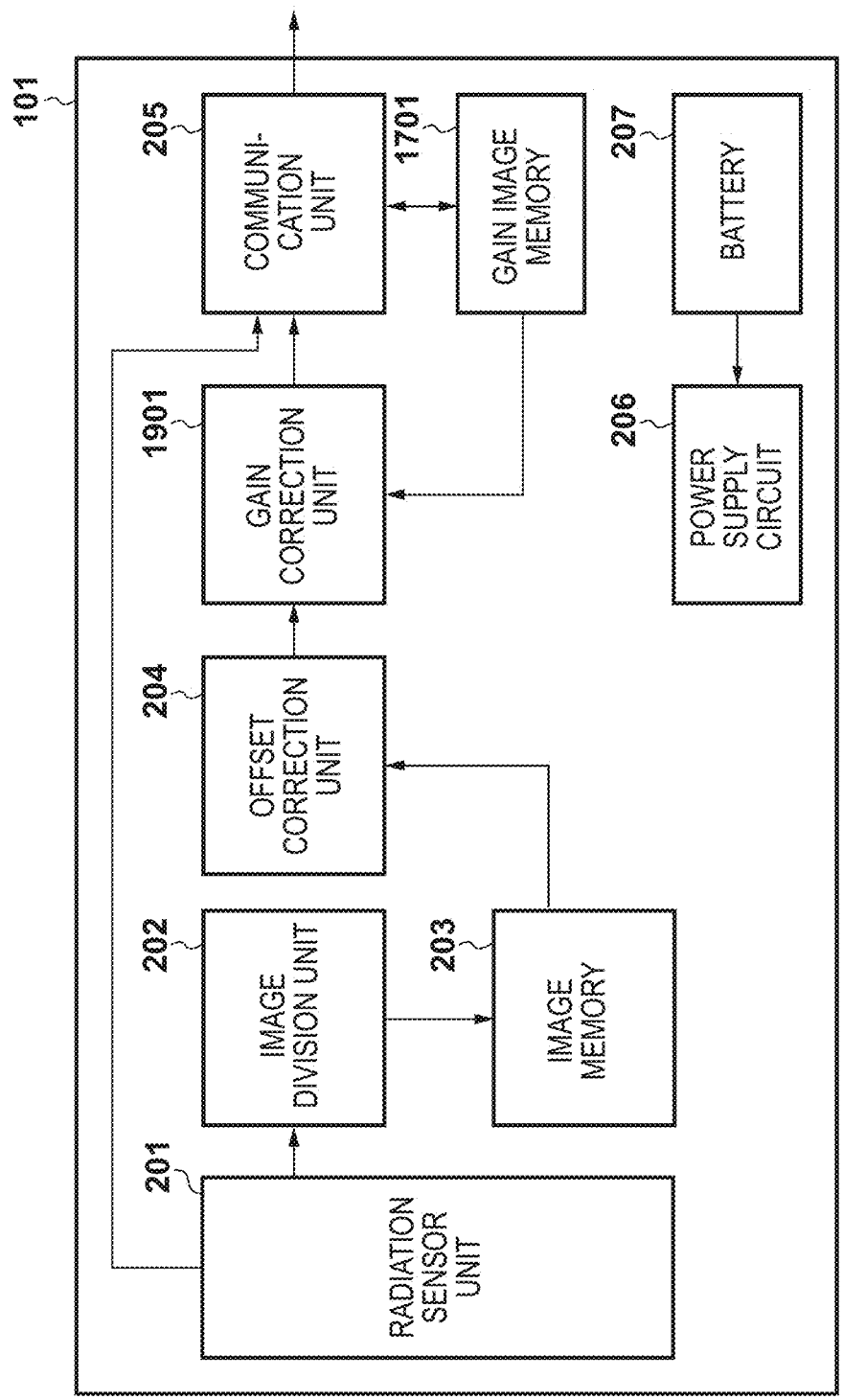
FIG. 19 is a block diagram showing an example of the arrangement of a radiation imaging apparatus according to the fourth embodiment of the present invention.

Next, the fourth embodiment will be explained. FIG. 19 is a block diagram showing an example of the internal arrangement of a radiation imaging apparatus 101 according to the fourth embodiment. In the fourth embodiment, the radiation imaging apparatus 101 further includes a gain correction unit 1901, in addition to the arrangement shown in FIG. 17 according to the third embodiment. Generation of a gain image is performed by an image processing apparatus 105. The gain image is transmitted to the radiation imaging apparatus 101, and saved in a gain image memory 1701. An object is imaged, and the gain correction unit 1901 executes gain correction on the image having undergone offset correction by an offset correction unit 204, by performing calculation equivalent to division by the gain image read out from the gain image memory 1701. When this processing is executed by hardware, subtraction may be performed after converting both the image and gain image into logarithms based on a logarithm conversion table, in order to reduce an increase in hardware scale owing to the division circuit. As for the offset correction image and the gain image, when an image division unit 202 divides in advance an image into reduced images, as shown in FIG. 19, it is desirable to divide in advance even the gain image similarly to the reduced images, and hold the divided gain images in the gain image memory 1701.

When the image processing apparatus 105 continuously holds a gain image, the gain image memory 1701 may use a volatile memory such as a DRAM. In this case, every time the radiation imaging apparatus 101 is activated, a gain image is transmitted from the image processing apparatus 105 to the radiation imaging apparatus 101, and held in the gain image memory 1701. When the radiation imaging apparatus 101 continuously holds a gain image, the gain image memory 1701 may use a non-volatile memory such as a flash memory. In this case, when the image processing apparatus 105 generates a gain image, the gain image is transmitted to the radiation imaging apparatus 101, and saved in the gain image memory 1701. To shorten the gain image readout time in gain correction, a gain image may be loaded into a volatile memory such as a DRAM at the time of, for example, activating the radiation imaging apparatus 101. This embodiment has described an example in which the image processing apparatus 105 performs generation of a gain image, but the radiation imaging apparatus 101 may perform it, as in the second embodiment.

In the first to fourth embodiments, the radiation imaging apparatus 101 includes the image division unit 202, and the image processing apparatus 105 includes the divided image composition unit 1002 in order to increase the preview speed. However, this is not indispensable in the practice of the essence of the present invention. It is also possible to send radiation images and offset images to the image processing apparatus 105, and perform offset correction in the image processing apparatus 105. Prior to radiation imaging of an object, an offset image may be obtained in advance at the time of, for example, turning on the radiation imaging apparatus 101 or obtaining an imaging order, and offset correction may be performed using the offset image. Further, offset correction may be performed not in the radiation imaging apparatus 101 but in the image processing apparatus 105.

As described above, according to the present invention, in an imaging method in which irradiation with a radiation is detected from a change of a current inside the radiation imaging apparatus to obviate the need for communication between the radiation imaging apparatus and the radiation generation apparatus, even when a sensitivity correction image (gain image) is generated, a defect in the sensitivity correction image (gain image) can be removed. This can reduce an artifact generated by sensitivity correction processing.

In the above-described embodiments, a plurality of radiation images different in the position of a defect may be obtained, and the images of defect-free regions out of the plurality of radiation images may be adhered based on information representing the position of the defect, and then averaged to generate a sensitivity correction image. The pixel values of pixels at corresponding positions in the images of the defect-free regions may be averaged to equalize addition counts in the respective pixels of a sensitivity correction image to be generated.

Note that the processing is not limited to processing of creating a white image by adhesion processing and then performing averaging. Adhesion processing and averaging processing may be executed at once.

In general, when the addition count of a white image changes for each region, the random noise reduction ratio changes. However, the above-mentioned arrangement can uniform the random noise reduction ratio for each region.

According to the present invention, even when irradiation with a radiation is detected based on a change of a current inside the radiation imaging apparatus and imaging is performed, a defect-free sensitivity correction image can be generated.

Fifth Embodiment

Next, the fifth embodiment will be described.

As a detector that is used in a medical X-ray imaging apparatus and the like in order to observe the distribution of X-rays having passed through a human body, a large-size image sensor using a solid-state image sensor, called a flat panel detector (to be abbreviated as an FPD hereinafter), is used more popularly in recent years. In the X-ray imaging apparatus using the FPD, X-ray irradiation timings need to be synchronized between the FPD (or a personal computer (PC) or relay apparatus connected to the FPD) and an X-ray generation apparatus. To achieve this, communication is performed to establish synchronization between the FPD and the X-ray generation apparatus, and the FPD transfers obtained X-ray image data to an image processing apparatus such as a PC for the purpose of image processing and save.

The FPD, the image processing apparatus, and the X-ray generation apparatus that emits X-rays are generally connected using a cable or the like via an interface necessary for communication between them. In most cases, these apparatuses are connected by a wireless interface such as a wireless LAN for the purpose of easy installation and handling, and improvement of the degree of freedom of imaging.

Further, an X-ray imaging apparatus and the like have also been implemented, in which the FPD itself can detect the start of X-ray irradiation from the X-ray generation apparatus to obviate the need for synchronous communication between the FPD and the X-ray generation apparatus, and further improve installation and operability. Japanese Patent Laid-Open Nos. 2011-247605 and 2011-249891 describe such X-ray imaging apparatuses in which detection scanning of sequentially selecting the respective rows of the FPD and switching the ON state/OFF state is performed to detect a change of a current flowing inside the apparatus, thereby detecting the start of X-ray irradiation.

Figure 24B:
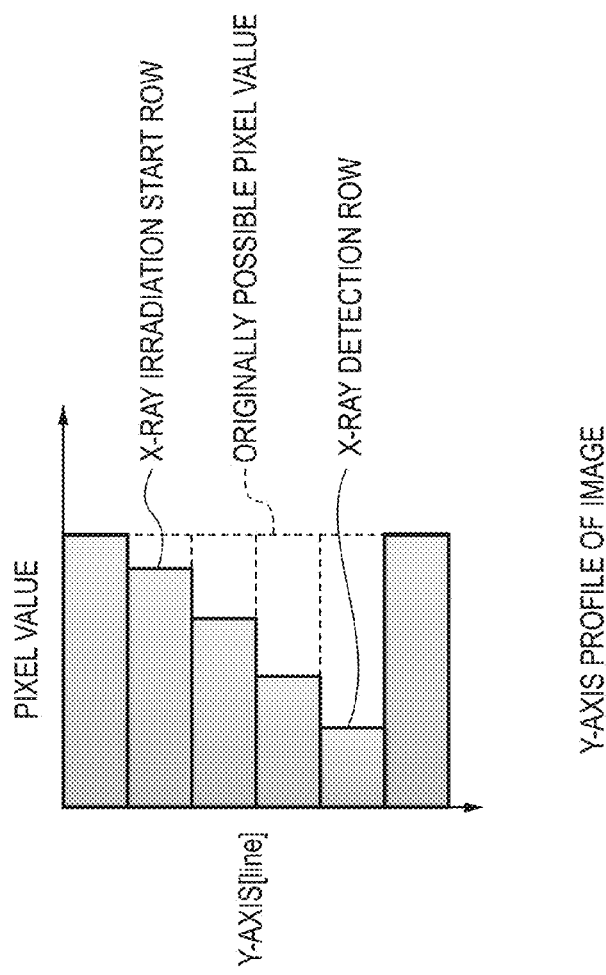
FIGS. 24A and 24B are views for explaining a detection delay artifact row.
Figure 24A:
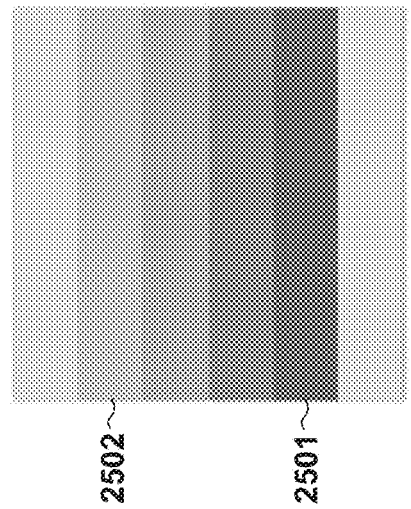

According to the X-ray irradiation start detection methods described in Japanese Patent Laid-Open Nos. 2011-247605 and 2011-249891, a time difference (detection delay) is generated until detection scanning for detecting the start of irradiation is stopped after X-ray irradiation actually starts and the X-ray imaging apparatus detects the start of irradiation. In a pixel of a row on which detection scanning has been executed within the range of this detection difference, some of charges generated by X-ray irradiation leak. As a result, a linear or wedged defect (this phenomenon will be referred to as a detection delay artifact hereinafter) may be generated in an X-ray image. FIGS. 24A and 24B show an example of a wedged detection delay artifact as a typical example. FIG. 24A shows an example of an image when the start of X-ray irradiation is automatically detected and imaging is executed. FIG. 24A shows that the pixel value decreases row by row between a row (an X-ray irradiation start row 502) on which detection scanning was executed at the start of actual X-ray irradiation, and a row (an X-ray detection row 501) on which the X-ray imaging apparatus detected the start of irradiation. FIG. 24B shows the Y-axis profile of FIG. 24A. In FIG. 24B, a pixel value indicated by a dotted line represents an originally possible pixel value when no detection delay artifact is generated.

As a measure against the detection delay artifact, Japanese Patent Laid-Open Nos. 2011-247605 and 2011-249891 propose to correct a detection delay artifact generated in an X-ray image by using the value of the current used to detect the start of X-ray irradiation.

In contrast, gain correction processing is performed on an obtained X-ray image in image processing after obtaining the X-ray image, in order to correct variations of the gains of pixels arising from nonuniformity by the deposition process of an X-ray detection sensor or the like, a singularly generated pixel with a different characteristic, aged deterioration or burn-in along with the use, or the like. As correction data used in gain correction, a gain image obtained by executing imaging by X-ray irradiation without arranging an object is used. Gain correction is executed by dividing, by a gain image, an X-ray image after offset correction (this is correction processing of removing or reducing a dark current component), and multiplying the obtained X-ray image by an appropriate coefficient such as the average value of the entire gain image.

However, when a gain image is sensed by the above-described method of detecting the start of X-ray irradiation, a detection delay artifact is similarly generated even in the gain image. When the detection delay artifact of the gain image is corrected by any image processing, a pixel in which the detection delay artifact is generated cannot correctly represent the original gain, and thus gain correction may not be performed correctly. If a gain image is obtained by a conventional method in which an X-ray imaging apparatus and an X-ray generation apparatus are connected to perform synchronous communication and perform imaging, the above-described detection delay artifact is not generated, but this method conflicts with the advantage in which connection is unnecessary. In the first place, the user may want to use the X-ray imaging apparatus in combination with an X-ray generation apparatus having no connection unit. In this situation, it is difficult to achieve both the imaging method of detecting the start of X-ray irradiation, and creation of a gain image by this imaging method.

An invention according to the fifth embodiment has been made in consideration of the above-described problem, and provides a technique capable of obtaining a high-accuracy gain image by using an image sensed by automatically detecting the start of irradiation with a radiation.

A radiation imaging system according to this embodiment corrects an artifact region generated by a radiation detection delay, and also performs gain correction for a radiation image obtained by imaging using a radiation detector constituted by a plurality of pixels. A gain image used in gain correction is created to reduce the influence of the artifact region generated by the radiation detection delay, implementing high-accuracy gain correction. Although an embodiment in a case in which X-rays are used as the radiation will be explained, the present invention is also applicable to even a radiation imaging apparatus other than the X-ray imaging apparatus.

FIG. 20 is a view showing an example of the arrangement of an X-ray imaging system according to this embodiment. An X-ray generation apparatus 2101 serving as a radiation generation apparatus emits X-ray rays toward an FPD 2102 serving as a radiation detector. The FPD 2102 and an image processing apparatus 2103 constitute an X-ray imaging apparatus, and the FPD 2102 transmits an image signal corresponding to a detected X-ray dose to the connected image processing apparatus 2103.

The image processing apparatus 2103 includes an I/O unit 2106 that performs data transmission/reception and the like, a CPU (Central Processing Unit) 2107 that controls various operations of the image processing apparatus 2103, and a memory 2108 in which programs to be executed by the CPU 2107 are stored, and various data and the like are read out and written. The image processing apparatus 2103 includes a storage medium 2109 for recording/saving image data and the like. A display apparatus 2104 that displays processing results, images, and the like, and an operation apparatus 2105 for accepting a user operation are connected to the image processing apparatus 2103.

Figure 21A:
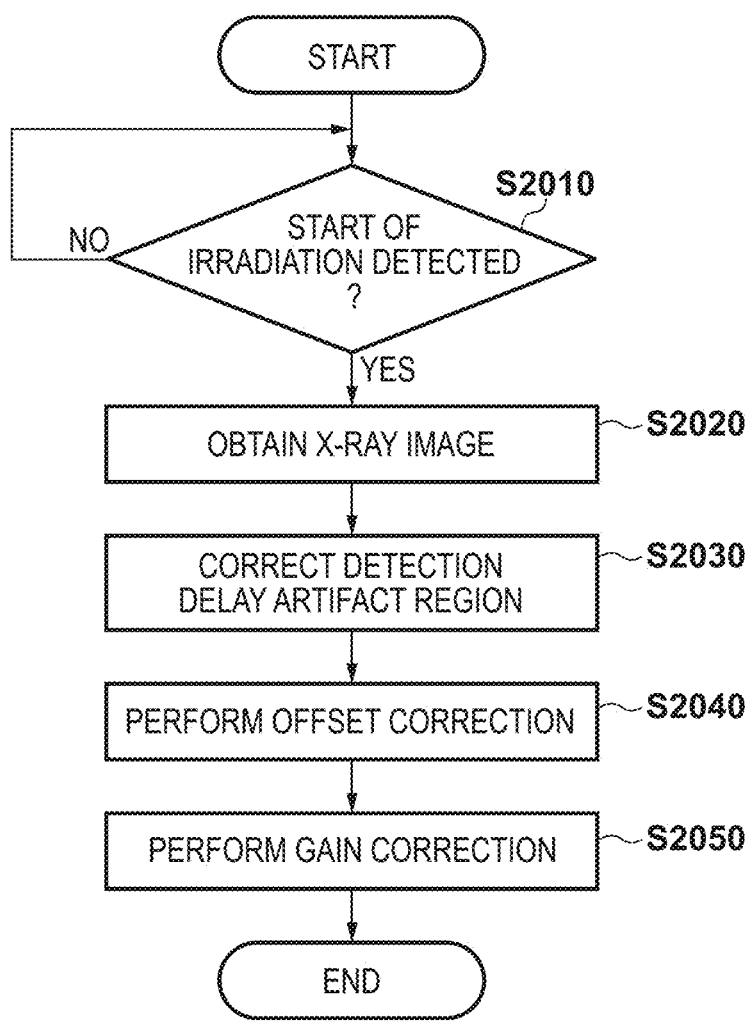
FIG. 21A is a flowchart showing X-ray imaging processing according to the fifth embodiment of the present invention.

X-ray imaging processing in the X-ray imaging system having the above arrangement will be explained. FIG. 21A is a flowchart for explaining X-ray imaging processing according to this embodiment. In step S2010, the CPU 2107 detects the start of X-ray irradiation based on a radiation dose (X-ray dose) detected in the FPD 2102. In this embodiment, the CPU 2107 detects the start of irradiation with a radiation based on X-ray doses sequentially read for respective rows from the FPD 2102. After the start of irradiation is detected, the CPU 2107 starts sensing of an X-ray image using the FPD 2102 (step S2020). In imaging, the FPD 2102 sends, to the I/O unit 2106 of the image processing apparatus 2103, X-ray image data (to be referred to as an original image hereinafter) obtained by converting an X-ray dose received by each internal X detection element into a digital signal. In step S2030, the CPU 2107 corrects image information of the region (detection delay artifact region) of an artifact generated in an original image owing to the time difference between the start of actual irradiation with a radiation and detection of the start of irradiation by, for example, the method described in Japanese Patent Laid-Open Nos. 2011-247605 and 2011-249891. After that, the CPU 2107 performs offset correction for removing a dark current component from the original image after artifact correction in step S2030 (step S2040), and performs gain correction using a gain image for the original image after offset correction (step S2050).

Next, processing of creating a gain image used in step S2050 will be explained. An outline of an operation in the X-ray imaging apparatus according to this embodiment when creating a gain image is as follows.

The operator designates creation of a gain image by using the operation apparatus 2105, and inputs an operation for starting imaging. This operation is an operation for exchanging information for imaging preparation between the FPD 2102 and the image processing apparatus 2103. The information for imaging preparation is information notifying the image processing apparatus of a state in which the FPD 2102 is capable of imaging. The state in which the FPD 2102 is capable of imaging indicates, for example, the completion of initialization processing of installed software, or the completion of a standby state until hardware changes from an unstable state upon power-on to a stable state.

The X-ray generation apparatus 2101 irradiates the FPD 2102 with a radiation in a state in which there is no shield (object). Upon receiving the X-rays, the FPD 2102 detects the start of X-ray irradiation, as in steps S2010 and S2020, and sends, to the I/O unit 2106 of the image processing apparatus 2103, image data (original image) obtained by converting an X-ray dose received by each internal X detection element into a digital signal. The image processing apparatus 2103 saves the received original image in the memory 2108 or the storage medium 2109. The CPU 2107 implements these internal processes of the image processing apparatus 2103. The image processing apparatus 2103 creates a gain image from the received original image (details of processing of creating a gain image will be described later with reference to the flowchart of FIG. 21B), and sends the processing result to the display apparatus 2104. Display of the processing result is, for example, display of a message that a gain image was created correctly, or display of a created gain image.

Next, the sequence of processing of creating a gain image will be explained in detail with reference to the flowchart of FIG. 21B. The processing of creating a gain image is constituted by base image obtaining processing (step S2100) of creating a plurality of sensed images (to be referred to as base images hereinafter) serving as the base of a gain image, and gain image obtaining processing (step S2200) of creating a gain image from the plurality of base images.

In base image obtaining processing (step S2100), creation of a base image is repetitively performed until a necessary number of base images for gain image creation are obtained. A plurality of base images necessary for gain image creation need to include two base images whose detection delay artifact regions do not overlap each other. When reducing a noise component such as quantization noise or noise in an electrical circuit, three or more base images are preferably created and used for gain image creation. The presence/absence of overlapping of detection delay artifact regions can be determined based on, for example, the position of a row in an image when the FPD 2102 detects the start of X-ray irradiation.

In this case, a row on which the start of irradiation was detected, and a predetermined number of immediately preceding rows on which detection scanning was performed may be determined as a detection delay artifact region. In this case, the predetermined number can be obtained from, for example, [time per row necessary for detection scanning]×[time difference until irradiation is detected after the start of actual irradiation]. The image processing apparatus 2103 may obtain the actual irradiation start time from the X-ray generation apparatus 2101. For example, the timepieces of the X-ray generation apparatus 2101 and image processing apparatus 2103 are synchronized, and information of the time when irradiation started is obtained from the X-ray generation apparatus. In this case, communication between the X-ray generation apparatus 2101 and the image processing apparatus 2103 is performed. Even in this case, communication between the X-ray generation apparatus 2101 and the FPD 2102 is unnecessary. The image processing apparatus 2103 receives, from the FPD 2102, the time when irradiation was detected. By calculating the difference between these two times, the image processing apparatus 2103 calculates the above-mentioned time difference. Alternatively, sensed base images may be displayed on the display apparatus 2104, and the user may determine overlapping of artifact regions.

The processing contents of base image obtaining processing (step S2100) will be explained. In step S2110, the image processing apparatus 2103 emits X-rays in a state in which there is no shield, and obtains a plurality of original images whose detection delay artifact regions do not overlap each other. Processing of automatically detecting the start of X-ray irradiation and performing imaging is the same as that described in steps S2010 and S2020. Then, in step S2120, the CPU 2107 performs offset correction processing in order to remove a dark current component from the original image. The offset correction processing is performed by, for example, after obtaining each original image, reading a dark current image from the FPD 2102 in a state in which no X-ray is emitted, and subtracting the dark current image from the original image. Note that the offset correction processing is not limited to this, and may be executed by, for example, reading a dark current image before imaging, and subtracting it from an original image. In this manner, a plurality of base images sensed in a state in which no object exists are obtained.

In gain image obtaining processing (step S2200), a gain image is created using two or more base images that have been created by the above-described processing and whose detection delay artifacts do not overlap each other. Gain image obtaining processing (step S2200) will be explained below.

First, in step S2210, the CPU 2107 performs discrimination processing of discriminating a detection delay artifact row constituting a detection delay artifact region in each base image obtained by base image obtaining processing (step S2100). In the detection delay artifact row discrimination processing, it is discriminated whether each row of each base image is a row on which a detection delay artifact has been generated. Details of the discrimination processing will be described later. In step S2220, the CPU 2107 performs normalization processing by using each base image and the discrimination processing result of the detection delay artifact row, thereby creating a normalized image. This normalization processing is performed to normalize an X-ray dose when each base image was sensed. In step S2230, the CPU 2107 creates a gain image by using the result of detection delay artifact row discrimination processing (step S2210) and the normalized image (step S2120).

Figure 22:
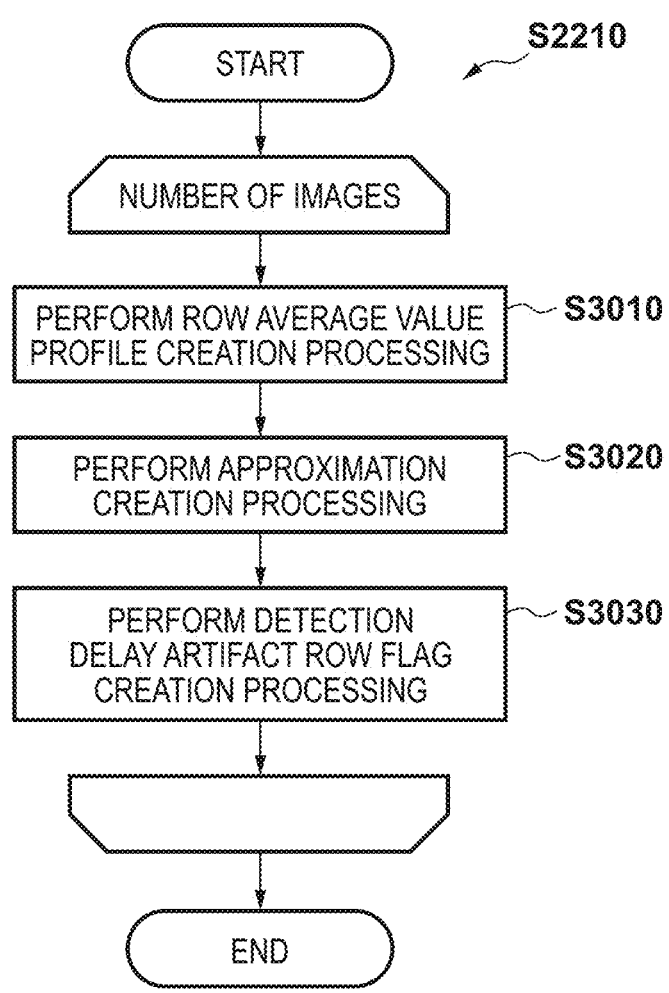
FIG. 22 is a flowchart showing processing of discriminating a detection delay artifact row.

Next, the detection delay artifact row discrimination processing (step S2210) will be explained in detail. FIG. 22 is a flowchart showing the detection delay artifact row discrimination processing (step S2210). As shown in FIG. 22, the discrimination processing includes profile creation processing (step S3010), approximation creation processing (step S3020), and flag creation processing (step S3030) for each individual base image. Note that the result of detection delay artifact row discrimination processing is used in normalization processing (step S2220) and gain image creation processing (step S2230) serving as subsequent processes.

First, in profile creation processing (step S3010), the CPU 2107 creates the profile of a feature amount calculated for each row in a base image. In this embodiment, the profile of the average value of the pixel values (luminance values) of pixels aligned in the row direction is created. Note that the feature amount is not limited to the average value of pixel values in a row, and may be another feature amount. For example, there are feature amounts obtained from a median and a frequency graph (histogram). Examples of the feature amount obtained from the histogram are an average value and a median after excluding 1% of frequencies on the large- and small-value sides. Next, in approximation creation processing (step S3020), the CPU 2107 creates, from the profile created in step S3010, an approximation representing an X-ray dose distribution input to the X-ray detector. More specifically, the CPU 2107 fits a model such as a quadratic expression or linear expression to the profile created in step S3010, and obtains an approximation by using the least squares method or the like. At this time, a detection delay artifact row takes a value not complying with the X-ray dose distribution, so a method capable of weighting an error, such as a robust estimation method, is preferably employed.

In flag creation processing (step S3030), the CPU 2107 discriminates whether each row of the base image is a detection delay artifact row, and records the discrimination result as a flag. In this embodiment, the CPU 2107 compares, for each row, the approximation derived by approximation creation processing (step S3020) and the profile of the row average value created by profile creation processing (step S3010). Then, the CPU 2107 determines, based on the comparison result, whether a detection delay artifact is generated. For example, when a row average value becomes equal to or smaller than a predetermined ratio with respect to a value represented by the approximation, it is determined that this row is a detection delay artifact row. The CPU 2107 stores, for example, the flag=1 in association with each row of the base image if this row is an artifact row, and stores the flag=0 if this row is not an artifact row.

An example using the approximation of the profile has been explained in the above-described discrimination processing, but the discrimination processing is not limited to this. For example, detection of a detection delay artifact row as described in base image obtaining processing (step S2100) may be used. More specifically, a row on which the start of irradiation was detected, and a predetermined number of rows immediately preceding this row in the reading order in detection scanning may be discriminated as detection delay artifact rows.

Next, the normalization processing (step S2220) in FIG. 21B will be explained in detail. FIG. 23 is a flowchart showing the sequence of normalization processing (step S2220). In this normalization processing, profile creation processing (step S4010), interpolation processing (step S4020), average value calculation processing step S2230, and normalized image creation processing (step S4040) are performed for each base image. Note that the normalization processing (step S2220) is performed to eliminate the influence of variations of the X-ray dose emitted by the X-ray generation apparatus 2101 in a plurality of base images by performing normalization using values from which the influence of the detection delay artifact is eliminated.

First, in profile creation processing (step S4010), the CPU 2107 creates the profile of the feature amount of each row. In this embodiment, the CPU 2107 creates the profile of the average value of a base image in the row direction. Note that this processing is the same as profile creation processing (step S3010) in detection delay artifact row discrimination processing, so the processing result in step S3010 may be used.

Figure 25:
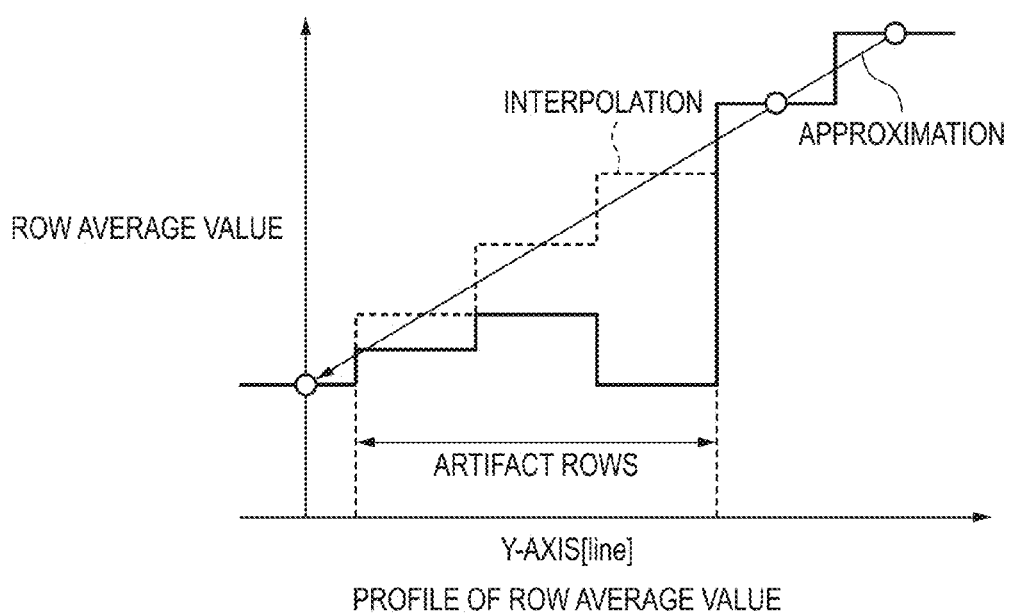
FIG. 25 is a graph for explaining interpolation processing of a profile on a detection delay artifact row.

Then, in interpolation processing (step S4020), the feature amount of the detection delay artifact region is interpolated and decided based on the feature amount of a region other than the detection delay artifact region. That is, the CPU 2107 decides by interpolation the row average value of rows discriminated as detection delay artifact rows by using the row average value of rows other than rows discriminated as detection delay artifact rows in the profile of the row average value created in profile creation processing (step S4010). In this way, an interpolated average value profile is created based on the average value of pixel values of respective rows other than the detection delay artifact region, and the interpolated values of rows of the detection delay artifact region. For example, as shown in FIG. 25, an approximation is created from the profile of the row average value excluding detection delay artifact rows, and the artifact rows are interpolated using the value of the approximation. The approximation may be a linear expression or a quadratic expression.

In average value calculation processing (step S4030), the CPU 2107 calculates the average value of the entire profile from the interpolated average value profile obtained by interpolation processing (step S4020). The average value of the profile obtained here can be handled as an average value free from the influence of detection delay artifact rows of the base image.

In normalized image creation processing (step S4040), the CPU 2107 normalizes the base image by using the average value calculated in average value calculation processing (step S4030), creating a normalized image. For example, the CPU 2107 obtains a normalized image by dividing the pixel value of each pixel of the base image by the average value calculated in average value calculation processing (step S4030).

Figure 21B:
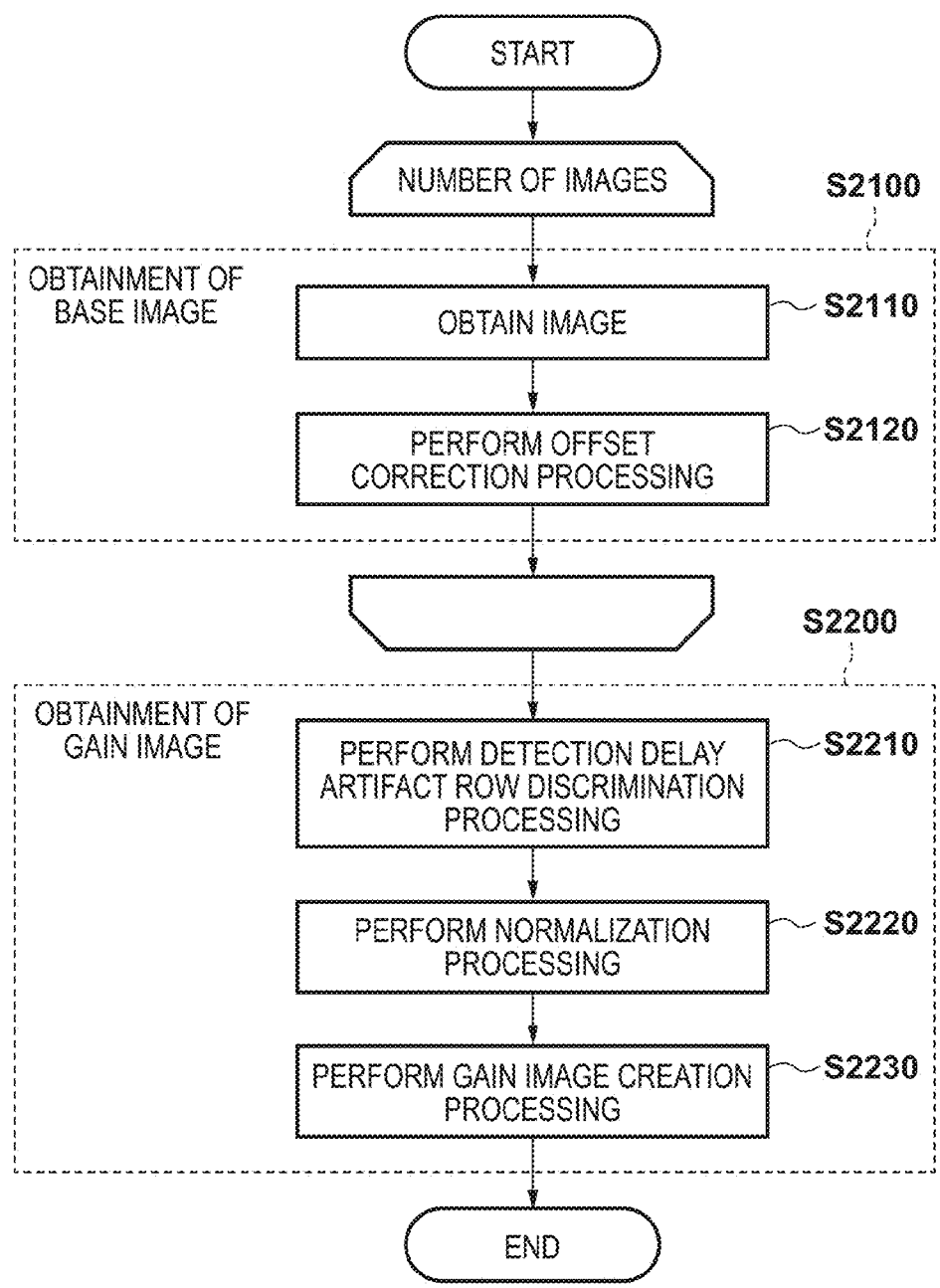
FIG. 21B is a flowchart showing gain image creation processing according to the fifth embodiment of the present invention.

In gain image creation processing (step S2230) of FIG. 21B, a gain image is created using a plurality of normalized images created in the above fashion. In this embodiment, the CPU 2107 creates a gain image for gain correction by compositing a plurality of normalized images without using image information of detection delay artifact rows discriminated in detection delay artifact row discrimination processing (step S2210). For example, the CPU 2107 creates a gain image by calculating, as a pixel value of a gain image, the average value of pixel values at the same coordinates in respective base images (normalized images) created in normalization processing (step S2220). At this time, the CPU 2107 does not use, for calculation of the average value, the pixel value of a row discriminated as a detection delay artifact row in discrimination processing (step S2210).

FIG. 26 is a view for explaining gain image creation processing. Assume that a first normalized image 2701 and a second normalized image 2721 are obtained as normalized images composited to create a gain image. A detection delay artifact region 2702 is detected in the first normalized image 2701, and a detection delay artifact region 2722 is detected in the second normalized image 2721. When creating a gain image 2741 by compositing these normalized images, the average value of pixels not belonging to the detection delay artifact regions is calculated and used as a pixel value of the gain image. For example, a pixel 2703 of the first normalized image 2701 and a pixel 2723 of the second normalized image 2721 are pixels at coordinates (x1, y1), and the average value of these pixel values serves as the pixel value of a pixel 2743 at the coordinates (x1, y1) in the gain image 2741. In the case of pixels 2704 and 2724 at coordinates (x2, y2), the pixel 2704 belongs to the detection delay artifact region and is not used for calculation of the average value. In this example, therefore, the pixel value of the pixel 2724 directly serves as the pixel value of a pixel 2744 in the gain image 2741. In the case of pixels 2705 and 2725 at coordinates (x3, y3), the pixel 2725 belongs to the detection delay artifact region and is not used for calculation of the average value, and the pixel value of the pixel 2705 directly serves as the pixel value of a pixel 2745 in the gain image 2741.

As described above, according to the fifth embodiment, a created gain image can correctly represent an original gain. Even if a detection delay artifact is generated, a gain image capable of appropriately executing gain correction can be obtained.

According to the present invention, a high-accuracy gain image can be obtained using an image sensed by automatically detecting the start of irradiation with a radiation.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-091999, filed Apr. 25, 2014 and 2014-159762, filed Aug. 5, 2014, which are hereby incorporated by reference herein in their entirety.

What is claimed is:

1. An image processing apparatus comprising:
one or more processors; and
one or more memories coupled to the one or more processors, the one or more memories having instructions stored thereon which, when executed by the one or more processors, cause the image processing apparatus to:
obtain a plurality of radiation images that have been sensed in the absence of an object to be irradiated and that include a defect, and information about the defect included in the radiation images; and
generate a sensitivity correction image without the defect based on the plurality of radiation images and the information about the defect.

2. The apparatus according to claim 1, wherein the instructions, when executed by the one or more processors, further cause the image processing apparatus to obtain the plurality of radiation images including the defect, and the information about the defect from a radiation imaging apparatus configured to detect irradiation with a radiation from a change of an internal current and transit to an image sensing state.

3. The apparatus according to claim 1, wherein the information about the defect includes information for specifying at least one of a position and width of a defect generated in a radiation image.

4. The apparatus according to claim 1, wherein the instructions, when executed by the one or more processors, further cause the image processing apparatus to determine, based on a relationship between defect position information of a first radiation image and defect position information of a second radiation image, whether the sensitivity correction image can be generated.

5. The apparatus according to claim 4, wherein the instructions, when executed by the one or more processors, further cause the image processing apparatus to determine, based on a relationship between the defect position information and defect width information of the first radiation image and the defect position information and defect width information of the second radiation image, whether the sensitivity correction image can be generated.

6. The apparatus according to claim 4, wherein when the image processing apparatus determines that the sensitivity correction image without the defect cannot be generated, the image processing apparatus newly obtains radiation images and information about a defect.

7. The apparatus according to claim 1, wherein the instructions, when executed by the one or more processors, further cause the image processing apparatus to generate a plurality of sensitivity correction images, and average the plurality of sensitivity correction images.

8. The apparatus according to claim 1, wherein the instructions, when executed by the one or more processors, further cause the image processing apparatus to perform sensitivity correction processing on the radiation image based on the generated sensitivity correction image.

9. The apparatus according to claim 8, wherein prior to the sensitivity correction processing, the image processing apparatus converts the sensitivity correction image and a radiation image to be corrected, into logarithms, respectively.

10. The apparatus according to claim 1, further comprising a transmission unit configured to transmit the generated sensitivity correction image to a radiation imaging apparatus.

11. The apparatus according to claim 1, wherein the instructions, when executed by the one or more processors, further cause the image processing apparatus to notify a user via a display apparatus of an operation necessary to generate the sensitivity correction image.

12. The apparatus according to claim 1, wherein the instructions, when executed by the one or more processors, further cause the image processing apparatus to:
obtain a plurality of radiation images different in a position of the defect,
generate the sensitivity correction image by adhering images of regions not including the defect out of the plurality of radiation images based on information representing the position of the defect, and averaging the images, and average pixel values of pixels at corresponding positions out of the images of the regions to equalize addition counts in respective pixels of the sensitivity correction image to be generated.

13. A radiation imaging apparatus that detects irradiation with a radiation from a change of an internal current and transits to an image sensing state, comprising:

one or more processors; and one or more memories coupled to the one or more processors, the one or more memories having instructions stored thereon which, when executed by the one or more processors, cause the radiation imaging apparatus to:

obtain a plurality of radiation images that have been sensed in the absence of an object to be irradiated and that include a defect, and information about the defect included in the radiation images; and generate a sensitivity correction image without the defect based on the plurality of radiation images and the information about the defect.

14. The apparatus according to claim 13, further comprising a detection unit configured to detect a change of the internal current while performing scanning of sequentially selecting sensors for respective rows in accordance with a predetermined condition, and switching an ON state/OFF state, wherein the information about the defect includes information representing a number of a row scanned at time when the internal current exhibited a predetermined change.

15. The apparatus according to claim 13, further comprising a non-volatile memory configured to hold the sensitivity correction image.

16. A radiation imaging system including a radiation generation apparatus that generates and emits a radiation, a radiation imaging apparatus that detects irradiation with a radiation from a change of an internal current and transits to an image sensing state, and an image processing apparatus that performs predetermined processing on a radiation image obtained from the radiation imaging apparatus, comprising:

one or more processors; and one or more memories coupled to the one or more processors, the one or more memories having instructions stored thereon which, when executed by the one or more processors, cause the radiation imaging apparatus to:

obtain a plurality of radiation images that have been sensed in the absence of an object to be irradiated and that include a defect, and information about the defect included in the radiation images; and generate a sensitivity correction image without the defect based on the plurality of radiation images and the information about the defect.

17. The system according to claim 16, wherein when the image processing apparatus does not hold a sensitivity correction image of the radiation imaging apparatus, when the radiation imaging apparatus holds the sensitivity correction image, the image processing apparatus obtains the sensitivity correction image from the radiation imaging apparatus, and when the radiation imaging apparatus does not hold the sensitivity correction image, the image processing apparatus generates a sensitivity correction image.

18. The system according to claim 17, wherein the radiation imaging apparatus and the sensitivity correction image corresponding to the radiation imaging apparatus are managed by adding unique identification information, and whether the radiation imaging apparatus holds the sensitivity correction image is determined based on the identification information.

19. The system according to claim 17, wherein imaging by the radiation imaging apparatus is inhibited during a determination operation of whether the radiation imaging apparatus holds a sensitivity correction image.

20. The system according to claim 16, wherein the radiation imaging apparatus divides a radiation image into a plurality of reduced images each having a small number of pixels for each pixel position in accordance with a predetermined condition, and sequentially transmits the reduced images to the image processing apparatus, and the image processing apparatus reconstructs a plurality of types of preview images different in resolution, and the image before division based on the plurality of reduced images received from the radiation imaging apparatus.

21. A method for controlling an image processing apparatus, comprising:

obtaining a plurality of radiation images that have been sensed in the absence of an object to be irradiated and that include a defect, and information about the defect included in the radiation images; and generating a sensitivity correction image without the defect based on the plurality of radiation images and the information about the defect.

22. A method for controlling a radiation imaging apparatus that detects irradiation with a radiation from a change of an internal current and transits to an image sensing state, comprising:

obtaining a plurality of radiation images that have been sensed in the absence of an object to be irradiated and that include a defect, and information about the defect included in the radiation images; and generating a sensitivity correction image without the defect based on the plurality of radiation images and the information about the defect.

23. A non-transitory computer-readable storage medium storing a computer program for causing a computer to execute the steps of the method for controlling an image processing apparatus according to claim 21.

24. A non-transitory computer-readable storage medium storing a computer program for causing a computer to execute the steps of the method for controlling a radiation imaging apparatus according to claim 22.

* * * * *